US012357456B2

(12) United States Patent
Tamir et al.

(10) Patent No.: US 12,357,456 B2
(45) Date of Patent: Jul. 15, 2025

(54) DEVICES AND METHODS FOR CRIMPING PROSTHETIC IMPLANTS

(71) Applicant: Edwards Lifesciences Corporation, Irvine, CA (US)

(72) Inventors: Ilan Tamir, Irvine, CA (US); Vipul P. Rajpara, Lake Forest, CA (US); Jonathan Roth, Pardes-Hanna Karkur (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1115 days.

(21) Appl. No.: 17/074,868

(22) Filed: Oct. 20, 2020

(65) Prior Publication Data

US 2021/0030533 A1 Feb. 4, 2021

Related U.S. Application Data

(63) Continuation of application No. PCT/US2019/028831, filed on Apr. 24, 2019.

(60) Provisional application No. 62/664,532, filed on Apr. 30, 2018.

(51) Int. Cl.
*A61F 2/24* (2006.01)
*A61F 2/95* (2013.01)
*A61L 2/00* (2006.01)

(52) U.S. Cl.
CPC ............ *A61F 2/243* (2013.01); *A61F 2/9522* (2020.05); *A61F 2/9524* (2020.05); *A61L 2/0094* (2013.01)

(58) Field of Classification Search
CPC ...... A61F 2/243; A61F 2/9522; A61F 2/9524; A61F 2/2433; A61F 2/2436; A61F 2/2466; A61F 2002/9505; A61L 2/0094
See application file for complete search history.

(56) References Cited

U.S. PATENT DOCUMENTS

| | | |
|---|---|---|
| 1,438,681 A | 12/1922 | Bath |
| 1,493,515 A | 5/1924 | Berthold |
| 2,079,498 A | 5/1937 | Douglas |
| 2,664,996 A | 1/1954 | Andrews |
| 2,787,925 A | 4/1957 | Buchanan et al. |
| 2,974,367 A | 3/1961 | Doering et al. |

(Continued)

FOREIGN PATENT DOCUMENTS

| | | |
|---|---|---|
| DE | 9034 C | 3/1880 |
| DE | 19532846 A1 | 3/1997 |

(Continued)

OTHER PUBLICATIONS http://www.machinesolutions.org/custom.sub.-tools.sub.--equipment/HV200.s-ub.--specs.htm, 1 page, Aug. 22, 2006.

*Primary Examiner* — Melanie R Tyson
*Assistant Examiner* — Rachel S Highland
(74) *Attorney, Agent, or Firm* — Klarquist Sparkman, LLP; Linda Allyson Nassif

(57) ABSTRACT

An assembly includes a holder device and a non-self-expandable prosthetic heart valve. The prosthetic heart valve can be radially compressed from an expanded configuration to a compressed configuration. The holder device is configured to hold the prosthetic heart valve in the expanded configuration and to allow the prosthetic heart valve to be inserted in a crimping device so that the prosthetic heart valve can be crimped onto a valve mounting portion of a delivery apparatus.

19 Claims, 21 Drawing Sheets

(56) References Cited

U.S. PATENT DOCUMENTS

| | | |
|---|---|---|
| 3,154,978 A | 11/1964 | Baker |
| 3,307,451 A | 3/1967 | Schuetz |
| 3,417,598 A | 12/1968 | Valente |
| 3,695,087 A | 10/1972 | Tuberman |
| 4,035,849 A | 7/1977 | Angell et al. |
| 4,308,744 A | 1/1982 | Baker |
| 4,350,036 A | 9/1982 | Valente |
| 4,454,657 A | 6/1984 | Yasumi |
| 4,578,982 A | 4/1986 | Schrock |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |
| 5,261,263 A | 11/1993 | Whitesell |
| 5,266,073 A | 11/1993 | Wall |
| 5,325,845 A | 7/1994 | Adair |
| 5,358,496 A | 10/1994 | Ortiz et al. |
| 5,411,521 A | 5/1995 | Putnam et al. |
| 5,411,552 A | 5/1995 | Andersen et al. |
| 5,437,083 A | 8/1995 | Williams et al. |
| 5,554,185 A | 9/1996 | Block et al. |
| 5,591,195 A | 1/1997 | Taheri et al. |
| 5,599,305 A | 2/1997 | Hermann et al. |
| 5,626,604 A | 5/1997 | Cottone, Jr. |
| 5,632,760 A | 5/1997 | Sheiban et al. |
| 5,639,274 A | 6/1997 | Fischell et al. |
| 5,728,068 A | 3/1998 | Leone et al. |
| 5,749,890 A | 5/1998 | Shaknovich |
| 5,749,921 A | 5/1998 | Lenker et al. |
| 5,782,809 A | 7/1998 | Umeno et al. |
| 5,810,873 A | 9/1998 | Morales |
| 5,824,044 A | 10/1998 | Quiachon et al. |
| 5,836,952 A | 11/1998 | Davis et al. |
| 5,840,081 A | 11/1998 | Andersen et al. |
| 5,893,852 A | 4/1999 | Morales |
| 5,908,405 A | 6/1999 | Imran et al. |
| 5,913,871 A | 6/1999 | Werneth et al. |
| 5,916,147 A | 6/1999 | Boury |
| 5,918,511 A | 7/1999 | Sabbaghian et al. |
| 5,951,540 A | 9/1999 | Verbeek |
| 5,961,536 A | 10/1999 | Mickley et al. |
| 5,968,068 A | 10/1999 | Dehdashtian et al. |
| 5,992,000 A | 11/1999 | Humphrey et al. |
| 6,007,543 A | 12/1999 | Ellis et al. |
| 6,009,614 A | 1/2000 | Morales |
| 6,019,777 A | 2/2000 | Mackenzie |
| 6,027,510 A | 2/2000 | Alt |
| 6,033,381 A | 3/2000 | Kontos |
| 6,051,002 A | 4/2000 | Morales |
| 6,074,381 A | 6/2000 | Dinh et al. |
| 6,082,990 A | 7/2000 | Jackson et al. |
| 6,125,523 A | 10/2000 | Brown et al. |
| 6,143,016 A | 11/2000 | Bleam et al. |
| 6,162,208 A | 12/2000 | Hipps |
| 6,167,605 B1 | 1/2001 | Morales |
| 6,168,614 B1 | 1/2001 | Andersen et al. |
| 6,174,327 B1 | 1/2001 | Mertens et al. |
| 6,176,116 B1 | 1/2001 | Wilhelm et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,309,383 B1 | 10/2001 | Campbell et al. |
| 6,352,547 B1 | 3/2002 | Brown et al. |
| 6,360,577 B2 | 3/2002 | Austin |
| 6,364,870 B1 | 4/2002 | Pinchasik |
| 6,379,372 B1 | 4/2002 | Dehdashtian et al. |
| 6,383,171 B1 | 5/2002 | Gifford et al. |
| 6,387,117 B1 | 5/2002 | Arnold, Jr. et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,558,418 B2 | 5/2003 | Carpentier et al. |
| 6,579,305 B1 | 6/2003 | Lashinski |
| 6,582,462 B1 | 6/2003 | Andersen et al. |
| 6,618,921 B1 | 9/2003 | Thornton |
| 6,629,350 B2 | 10/2003 | Motsenbocker |
| 6,651,478 B1 | 11/2003 | Kokish |
| 6,652,578 B2 | 11/2003 | Bailey et al. |
| 6,682,553 B1 | 1/2004 | Webler, Jr. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,769,161 B2 | 8/2004 | Brown et al. |
| 6,823,576 B2 | 11/2004 | Austin |
| 6,830,584 B1 | 12/2004 | Seguin |
| 6,840,081 B2 | 1/2005 | Kokish |
| 6,889,579 B1 | 5/2005 | Brown |
| 6,893,460 B2 | 5/2005 | Spenser et al. |
| 6,908,481 B2 | 6/2005 | Cribier |
| 6,915,560 B2 | 7/2005 | Austin |
| 6,920,674 B2 | 7/2005 | Thornton |
| 6,925,847 B2 | 8/2005 | Motsenbocker |
| 6,931,899 B2 | 8/2005 | Goff et al. |
| 6,968,607 B2 | 11/2005 | Motsenbocker |
| 6,988,881 B2 | 1/2006 | Motsenbocker et al. |
| 7,010,953 B2 | 3/2006 | Stupecky |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,021,114 B2 | 4/2006 | Perreault |
| 7,069,794 B2 | 7/2006 | Motsenbocker et al. |
| 7,096,554 B2 | 8/2006 | Austin et al. |
| 7,137,993 B2 | 11/2006 | Acosta et al. |
| 7,143,625 B2 | 12/2006 | Edin |
| 7,152,452 B2 | 12/2006 | Kokish |
| 7,207,204 B2 | 4/2007 | Weber et al. |
| 7,225,518 B2 | 6/2007 | Eidenschink et al. |
| 7,276,084 B2 | 10/2007 | Yang et al. |
| 7,284,401 B2 | 10/2007 | Larson et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,389,670 B1 | 6/2008 | Kokish et al. |
| 7,393,360 B2 | 7/2008 | Spenser et al. |
| 7,415,861 B2 | 8/2008 | Sokel |
| 7,435,257 B2 | 10/2008 | Lashinski et al. |
| 7,487,579 B2 | 2/2009 | Eidenschink et al. |
| 7,510,575 B2 | 3/2009 | Spenser et al. |
| 7,530,253 B2 | 5/2009 | Spenser et al. |
| 7,585,321 B2 | 9/2009 | Cribier |
| 7,587,801 B2 | 9/2009 | Austin |
| 7,594,926 B2 | 9/2009 | Linder et al. |
| 7,597,709 B2 | 10/2009 | Goodin |
| 7,618,446 B2 | 11/2009 | Andersen et al. |
| 7,628,051 B1 | 12/2009 | Kokish et al. |
| 7,780,723 B2 | 8/2010 | Taylor |
| 7,785,366 B2 | 8/2010 | Maurer et al. |
| 7,892,201 B1 | 2/2011 | Laguna et al. |
| 7,895,876 B2 | 3/2011 | Spenser et al. |
| 7,959,661 B2 | 6/2011 | Hijlkema et al. |
| 7,967,138 B2 | 6/2011 | Ryan et al. |
| 8,006,535 B2 | 8/2011 | Righini et al. |
| 8,029,556 B2 | 10/2011 | Rowe |
| 8,112,857 B2 | 2/2012 | Voelkl |
| 8,167,932 B2 | 5/2012 | Bourang et al. |
| 8,312,614 B2 | 11/2012 | Sokel |
| RE43,882 E | 12/2012 | Hopkins et al. |
| 8,449,606 B2 | 5/2013 | Eliasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,788,931 B2* | 10/2017 | Giordano .............. A61F 2/2427 |
| 9,795,477 B2 | 10/2017 | Tran et al. |
| 9,937,038 B2* | 4/2018 | Murphy .................. A61F 2/95 |
| 10,245,145 B2* | 4/2019 | Mantanus ............ A61F 2/2436 |

(56) References Cited

U.S. PATENT DOCUMENTS

| | | | |
|---|---|---|---|
| 2001/0002445 A1 | 5/2001 | Vesely | |
| 2001/0007082 A1 | 7/2001 | Dusbabek et al. | |
| 2001/0044608 A1* | 11/2001 | Odell | A61M 5/3202 604/199 |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2003/0192164 A1 | 10/2003 | Austin | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0004575 A1* | 1/2005 | Sgro | A61B 17/064 606/220 |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno-Azizi | |
| 2006/0025857 A1 | 2/2006 | Bergheim et al. | |
| 2006/0213049 A1 | 9/2006 | Serrano et al. | |
| 2006/0282150 A1 | 12/2006 | Olson et al. | |
| 2007/0005131 A1 | 1/2007 | Taylor | |
| 2007/0056346 A1 | 3/2007 | Spenser et al. | |
| 2007/0061009 A1* | 3/2007 | Spenser | A61F 2/2412 623/2.11 |
| 2007/0073389 A1 | 3/2007 | Bolduc et al. | |
| 2007/0088431 A1 | 4/2007 | Bourang et al. | |
| 2007/0112422 A1 | 5/2007 | Dehdashtian | |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0125853 A1 | 5/2008 | Bailey et al. | |
| 2008/0288077 A1* | 11/2008 | Reo | A61F 2/442 623/17.11 |
| 2008/0294230 A1 | 11/2008 | Parker | |
| 2009/0024428 A1 | 1/2009 | Hudock, Jr. | |
| 2009/0043249 A1 | 2/2009 | Sokel | |
| 2009/0054976 A1* | 2/2009 | Tuval | A61F 2/2427 623/2.11 |
| 2009/0069889 A1 | 3/2009 | Suri et al. | |
| 2009/0131864 A1* | 5/2009 | Pickhard | A61M 5/284 604/83 |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2010/0292780 A1* | 11/2010 | Straubinger | A61F 2/95 623/1.23 |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0101569 A1 | 4/2012 | Mearns et al. | |
| 2012/0123529 A1 | 5/2012 | Levi et al. | |
| 2012/0239142 A1 | 9/2012 | Liu et al. | |
| 2013/0030519 A1 | 1/2013 | Tran et al. | |
| 2013/0261742 A1* | 10/2013 | Gaschino | A61F 2/0095 623/2.11 |
| 2013/0317598 A1 | 11/2013 | Rowe et al. | |
| 2014/0215791 A1* | 8/2014 | Soundararajan | A61F 2/9524 29/700 |
| 2014/0296962 A1 | 10/2014 | Cartledge et al. | |
| 2015/0336150 A1* | 11/2015 | Peterson | A61F 2/2418 72/429 |
| 2017/0065415 A1 | 3/2017 | Rupp et al. | |
| 2018/0153689 A1 | 6/2018 | Maimon et al. | |
| 2018/0344456 A1 | 12/2018 | Barash et al. | |
| 2018/0344490 A1* | 12/2018 | Fox | B23P 19/02 |

FOREIGN PATENT DOCUMENTS

| | | |
|---|---|---|
| DE | 19907646 A1 | 8/2000 |
| EP | 0592410 B1 | 10/1995 |
| EP | 0850607 A1 | 7/1998 |
| EP | 2644158 A1 | 10/2013 |
| FR | 2815844 A1 | 5/2002 |
| WO | 9117720 A1 | 11/1991 |
| WO | 9414573 A1 | 7/1994 |
| WO | 9829057 A1 | 7/1998 |
| WO | 9912483 A1 | 3/1999 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 02060352 | 8/2002 |
| WO | 03030776 A2 | 4/2003 |
| WO | 03047468 A1 | 6/2003 |
| WO | 2004019825 A1 | 3/2004 |
| WO | 2005084595 A1 | 9/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |
| WO | 2016046599 A1 | 3/2016 |
| WO | 2018226475 A1 | 12/2018 |

* cited by examiner

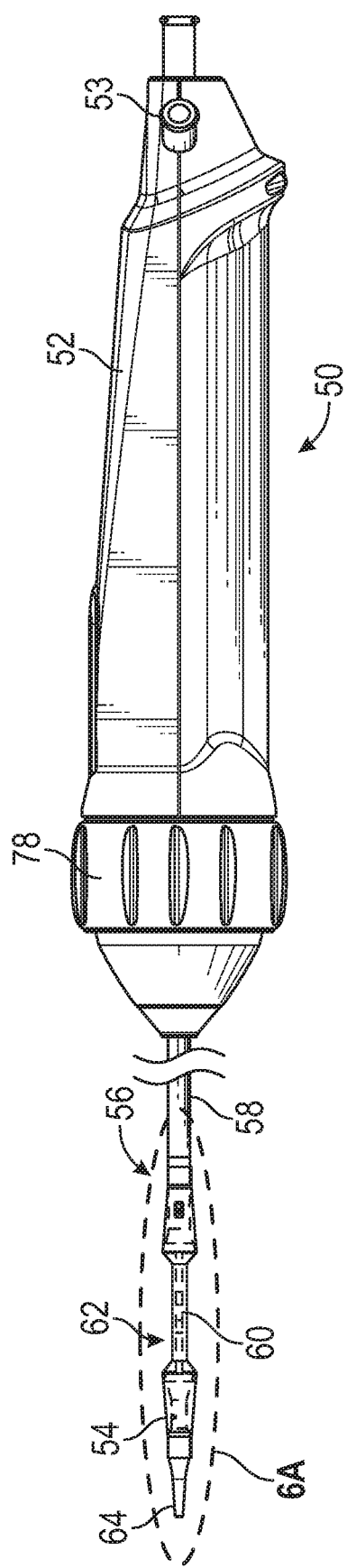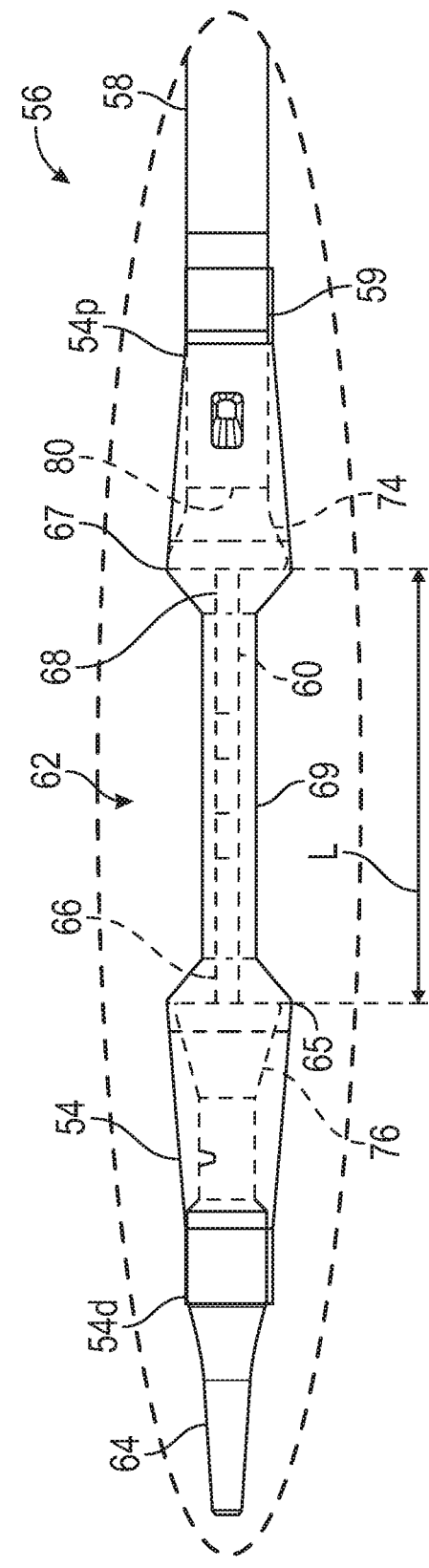
FIG. 3A
FIG. 3B

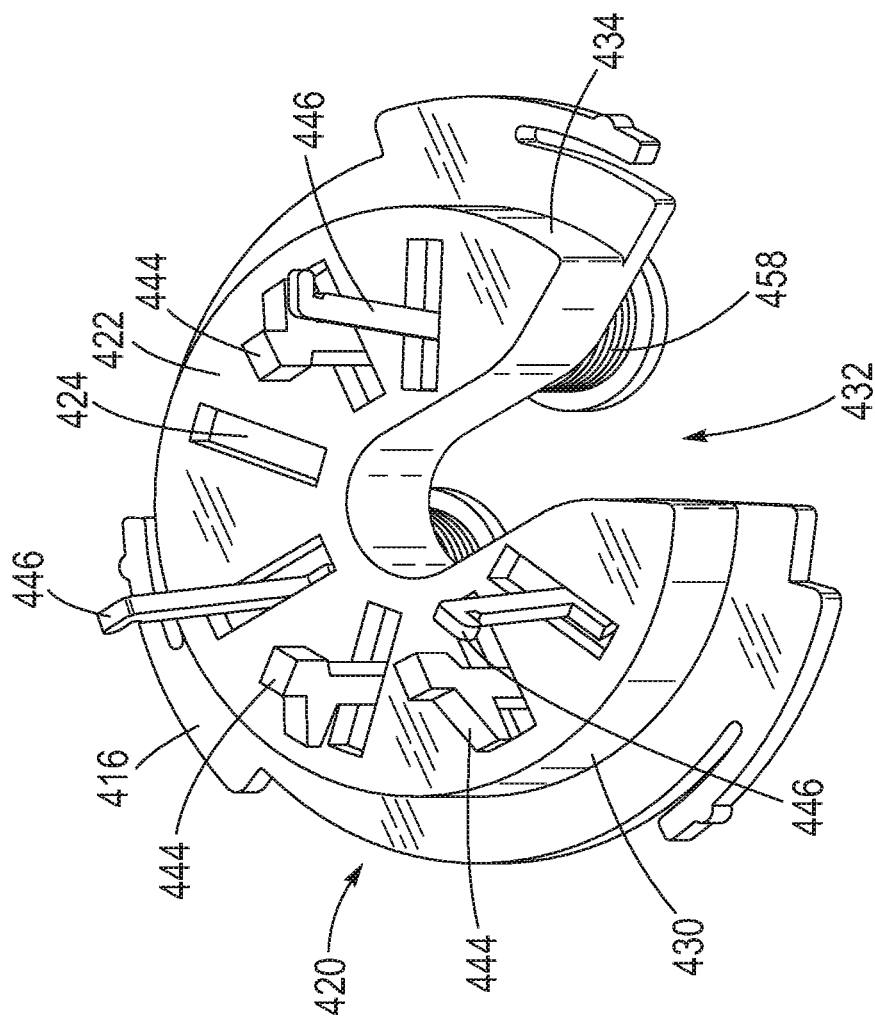
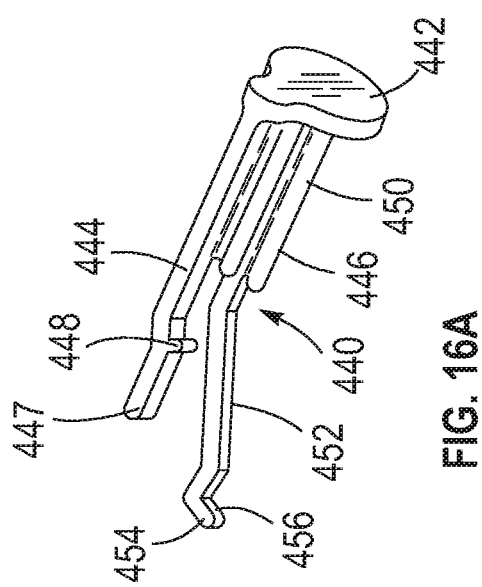
FIG. 16B
FIG. 16A

DEVICES AND METHODS FOR CRIMPING PROSTHETIC IMPLANTS

CROSS REFERENCE TO RELATED APPLICATIONS

This application is a continuation of International Application No. PCT/US2019/028831, filed Apr. 24, 2019, which claims the benefit of U.S. Provisional Application No. 62/664,532, filed Apr. 30, 2018, each of which is incorporated by reference herein.

FIELD

The present application pertains generally to devices and related methods for crimping prosthetic implants, such as prosthetic heart valves.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic heart valve is configured to be implanted in a much less invasive procedure by way of catheterization. For example, collapsible transcatheter prosthetic heart valves can be compressed or crimped and percutaneously introduced in the compressed state with a delivery apparatus and expanded to a functional size at the desired position.

Such transcatheter prosthetic valves may be self-expandable or balloon-expandable. Balloon-expandable prosthetic valves are typically crimped from an initial large diameter to a smaller diameter prior to advancement to a treatment site in the body. Before crimping, a balloon expandable prosthetic valve is typically placed over an inflatable balloon on a catheter shaft. Once delivered to the implantation site, the balloon can be inflated to expand the prosthetic valve to its functional size. Self-expanding prosthetic valves are typically also crimped to a smaller diameter, but are then inserted into a sheath. After placement in the body, the sheath is retracted, and the prosthetic valve expands inside the body.

SUMMARY

Disclosed herein are exemplary embodiments of devices, systems and related methods for crimping a prosthetic implants onto a delivery apparatus, which can be used to deliver the crimped prosthetic implant to a deployment site within a body of a subject. In some implementations, the delivery apparatus can be used to deliver a prosthetic implant through the vasculature, such as to a heart of the subject.

Certain embodiments of the disclosure concern an assembly including a holder device and a non-self-expandable prosthetic heart valve. The prosthetic heart valve can be radially compressed from an expanded configuration to a compressed configuration. The holder device can be configured to hold the prosthetic heart valve in the expanded configuration and to allow the prosthetic heart valve to be inserted in a crimping device so that the prosthetic heart valve can be crimped onto a valve mounting portion of a delivery apparatus.

In some embodiments, the holder device can include one or more retaining members configured to secure the prosthetic heart valve to the holder device when the prosthetic heart valve is in the expanded configuration and configured to release the prosthetic heart valve from the holder device when the prosthetic heart valve is compressed from the expanded configuration to the compressed configuration on the valve mounting portion of the delivery apparatus.

In some embodiments, a distal portion of each retaining member can extend distally into the prosthetic heart valve when the prosthetic heart valve is in the expanded configuration. The distal portion of each retaining member can be disposed proximal to the prosthetic heart valve when the prosthetic heart valve is in the compressed configuration.

In some embodiments, each of the retaining members can have a protrusion extending radially outwardly at a distal end of the retaining member. Each protrusion can be configured to extend radially outwardly into an opening of the prosthetic heart valve when the prosthetic heart valve is in the expanded configuration.

In some embodiments, the holder device can include a first portion and a second portion. The one or more retaining members can extend distally from the second portion and be axially moveable relative to a distal face of the first portion.

In some embodiments, the prosthetic heart valve can elongate unidirectionally when the prosthetic heart valve is crimped from the expanded configuration to the compressed configuration such that the prosthetic heart valve can elongate distally while the distal face of the first portion prevents proximal elongation of the prosthetic heart valve.

In some embodiments, the retaining members can be configured to extend distally relative to the distal face of the first portion for coupling to the prosthetic heart valve in the expanded configuration, and move proximally relative to the distal face of the first portion after releasing the prosthetic heart valve when the prosthetic heart valve is radially compressed.

In some embodiments, when the prosthetic heart valve is held by the holder device, a proximal end portion of the prosthetic heart valve can abut the distal face of the first portion when the prosthetic heart valve is in the expanded configuration and is secured to the holder device by the retaining members.

In some embodiments, the second portion of the holder device can include one or more sloped projections corresponding to the one or more retaining members, and wherein each sloped projection can interface with a sloped member on the corresponding retaining member such that the retaining members can slide distally into an interior space of the prosthetic heart valve when the prosthetic heart valve is in the expanded configuration.

In some embodiments, the holder device can include one or more biasing members configured to bias the second portion proximally relative to the first portion.

In some embodiments, the second portion can include one or more arms, wherein a distal end of each arm can extend distally relative to the distal face of the first portion when the retaining members are coupled to the prosthetic heart valve.

In some embodiments, at least one arm can be circumferentially disposed between a pair of adjacent retaining members. The retaining members can extend radially outwardly relative to the arms when the prosthetic heart valve is in the expanded configuration. The retaining members can be compressed radially inwardly and radially align with at least a portion of the arms as the prosthetic heart valve is radially compressed.

In some embodiments, the distal end of each arm can include a sloped surface configured to interface with a crimping jaw such that a radially inward movement of the crimping jaw can exert a force to the sloped surface and urge the corresponding arm to move proximally relative to the first portion.

In some embodiments, the assembly can further include a positioning device configured to be releasably coupled to a shaft of the delivery apparatus and to be releasably coupled to the holder device.

In some embodiments, the positioning device can include a body having an interior surface defining an axially extending passage that is sized to form an interference fit with a segment of the shaft.

In some embodiments, the segment of the shaft can be located distally by a predefined distance relative to the valve mounting portion.

In some embodiments, the inner surface of the body can include a row of a plurality of circumferentially oriented grooves extending from a proximal end of the body to a distal end of the body such that a sterilization gas can permeate into the passage through the plurality of grooves when the body is coupled to the shaft.

In some embodiments, the holder device can include one or more first coupling members that are mateable with one or more second coupling members of the positioning device.

In some embodiments, the assembly can further include the crimping device. The crimping device can be configured to radial compress the prosthetic heart valve from the expanded configuration to the compressed configuration. The holder device can include one or more third coupling members that are mateable with one or more fourth coupling members of the crimping device.

Certain embodiments of the disclosure also concern a system for prosthetic heart valve implantation. The system can include a positioning and holder assembly configured to retain a prosthetic heart valve in an expanded configuration, be mounted on a shaft of a delivery apparatus, and allow insertion of the prosthetic heart valve into a crimping device for crimping the prosthetic heart valve from a radially expanded configuration to a radially compressed configuration onto a valve mounting portion of the delivery apparatus.

In some embodiments, the positioning and holder assembly can include a positioning portion configured to be releasably coupled to the shaft of the delivery apparatus and a holder portion configured to be releasably retain the prosthetic heart valve in the radially expanded configuration while the prosthetic heart valve is crimped onto the valve mounting portion of the delivery apparatus.

In some embodiments, the positioning portion and the holder portion can be separable from each other.

In some embodiments, the positioning portion and the holder portion can be non-separable from each other.

In some embodiments, the holder portion can include one or more retaining members configured to secure the prosthetic heart valve to the holder portion when the prosthetic heart valve is in the expanded configuration and configured to release the prosthetic heart valve from the holder portion when the prosthetic heart valve is crimped from the expanded configuration to the compressed configuration on the valve mounting portion of the delivery apparatus.

In some embodiments, a distal portion of each retaining member can extend distally into the prosthetic heart valve when the prosthetic heart valve is in the expanded configuration. The distal portion of each retaining member can be disposed proximal to the prosthetic heart valve when the prosthetic heart valve is in the compressed configuration.

In some embodiments, each of the retaining members can have a protrusion extending radially outwardly at a distal end of the retaining member. Each protrusion can be configured to extend radially outwardly into an opening of the prosthetic heart valve when the prosthetic heart valve is in the expanded configuration.

In some embodiments, the holder portion can include a first portion and a second portion. The one or more retaining members can extend distally from the second portion and be axially moveable relative to a distal face of the first portion.

In some embodiments, the prosthetic heart valve can elongate unidirectionally when the prosthetic heart valve is crimped from the expanded configuration to the compressed configuration such that the prosthetic heart valve can elongate distally while the distal face of the first portion prevents proximal elongation of the prosthetic heart valve.

In some embodiments, the plurality of retaining members can be configured to extend distally relative to the distal face of the first portion for coupling to the prosthetic heart valve in the expanded configuration, and move proximally relative to the distal face of the first portion after releasing the prosthetic heart valve when the prosthetic heart valve is radially compressed.

In some embodiments, when the prosthetic heart valve is held by the holder portion, a proximal end portion of the prosthetic heart valve can abut the distal face of the first portion when the prosthetic heart valve is in the expanded configuration and is secured to the holder portion by the plurality of retaining members.

In some embodiments, the second portion can include a plurality of sloped projections corresponding to the plurality of retaining members. Each sloped projection can interface with a sloped member on the corresponding retaining member such that the retaining members can slide distally into an interior space of the prosthetic heart valve when the prosthetic heart valve is in the expanded configuration.

In some embodiments, the holder portion can include one or more biasing members configured to bias the second portion proximally relative to the first portion.

In some embodiments, the second portion can include one or more arms. A distal end of each arm can extend distally relative to the distal face of the first portion when the retaining members are coupled to the prosthetic heart valve.

In some embodiments, at least one arm can be circumferentially disposed between a pair of adjacent retaining members. The retaining members can extend radially outwardly relative to the arms when the prosthetic heart valve is in the expanded configuration. The retaining members can be compressed radially inwardly and radially align with at least a portion of the arms as the prosthetic heart valve is radially compressed.

In some embodiments, the distal end of each arm can include a sloped surface configured to interface with a crimping jaw of the crimping device such that a radially inward movement of the crimping jaw can exert a force to the sloped surface and urge the corresponding arm to move proximally relative to the first portion.

In some embodiments, the positioning portion can include a body having an interior surface defining an axially extending passage that is sized to form an interference fit with a segment of the shaft.

In some embodiments, the segment of the shaft can be located distally by a predefined distance relative to the valve mounting portion.

In some embodiments, the inner surface of the body can include a row of a plurality of circumferentially oriented grooves extending from a proximal end of the body to a distal end of the body such that a sterilization gas can permeate into the passage through the plurality of grooves when the body is coupled to the shaft.

In some embodiments, the positioning and holder assembly can further include one or more coupling members that are mateable to one or more complimentary coupling members of the crimping device.

Certain embodiments of the disclosure further concern a method of crimping a prosthetic heart valve onto a delivery apparatus. The method can include coupling a crimping device to a positioning and holder assembly mounted on a shaft of a delivery apparatus so that a prosthetic heart valve retained by the positioning and holder assembly is inserted into the crimping device, and actuating the crimping device to radially compress the prosthetic heart valve from an expanded configuration to a compressed configuration and onto a valve mounting portion of the delivery apparatus.

In some embodiments, the method can further include coupling the prosthetic heart valve in the expanded configuration to the positioning and holder assembly.

In some embodiments, the method can further include mounting the positioning and holder assembly to a predetermined location on the shaft of the delivery apparatus. The predetermined location can be spaced relative to the valve mounting portion of the delivery apparatus.

In some embodiments, the positioning and holder assembly can include a positioning portion releasably coupled to the shaft of the delivery apparatus and a holder portion releasably retaining the prosthetic heart valve.

In some embodiments, the act of mounting the positioning and holder assembly can include coupling the positioning portion to the predetermined location on the shaft of the delivery apparatus, and coupling the holder portion to the positioning device.

In some embodiments, the act of actuating the crimping device can release the prosthetic heart valve from the positioning and holder assembly.

In some embodiments, the compression of the prosthetic heart valve can cause unidirectional elongation of the prosthetic heart valve such that a proximal end portion of the prosthetic heart valve is fixedly aligned with a proximal end of the valve mounting portion and a distal end portion of the prosthetic heart valve extends distally during the compression until it aligns with a distal end of the valve mounting portion when the prosthetic heart valve is in the compressed configuration.

In some embodiments, the method can further include decoupling the positioning and holder assembly from the delivery apparatus after the prosthetic heart valve is crimped onto the valve mounting portion.

In some embodiments, the method can further include removing the delivery apparatus, together with the prosthetic heart valve, from the crimping device after the positioning and holder assembly is decoupled from the delivery apparatus.

In some embodiments, the positioning and holder assembly can include one or more retaining members configured to releasably couple to the prosthetic heart valve. The positioning and holder assembly can further include one or more arms. Each arm can extend distally into an interior space of the prosthetic heart valve when the retaining members are coupled to the prosthetic heart valve.

In some embodiments, the act of actuating the crimping device can push the one or more retaining members radially inwardly so as to decouple the one or more retaining members from the prosthetic heart valve.

In some embodiments, the act of actuating the crimping device can push the one or more arms proximally relative to and away from the prosthetic heart valve.

Certain embodiments of the disclosure also concern a holder device for a prosthetic heart valve. The holder device can include one or more retaining members configured to secure a prosthetic heart valve to the holder device when the prosthetic heart valve is in a radially expanded configuration and configured to release the prosthetic heart valve from the holder device when the prosthetic heart valve is compressed with a crimping device from the radially expanded configuration to a radially compressed configuration.

In some embodiments, each of the retaining members can have a protrusion extending radially outwardly at a distal end of the retaining member. Each protrusion can be configured to extend radially outwardly into an opening of the prosthetic heart valve when the prosthetic heart valve is in the expanded configuration.

In some embodiments, a distal portion of each retaining member can extend distally into the prosthetic heart valve when the prosthetic heart valve is in the expanded configuration. The distal portion of each retaining member can be disposed proximal to the prosthetic heart valve when the prosthetic heart valve is in the compressed configuration.

In some embodiments, the holder device can further includes a valve alignment portion configured to secure the holder device to the crimping device. The retaining members can be movable relative to a distal face of the valve alignment portion.

In some embodiments, a proximal end portion of the prosthetic heart valve can abut the distal face of the valve alignment portion when the prosthetic heart valve is in the expanded configuration.

In some embodiments, the holder device can further include one or more biasing members configured to bias the retaining members proximally relative to the valve alignment portion.

In some embodiments, the holder device can further include one or more arms. A distal end of each arm can extend distally relative to the distal face of the valve alignment portion when the retaining members are coupled to the prosthetic heart valve.

In some embodiments, at least one arm can be circumferentially disposed between a pair of adjacent retaining members. The retaining members can extend radially outwardly relative to the arms when the prosthetic heart valve is in the expanded configuration. The retaining members can be compressed radially inwardly and radially align with at least a portion of the arms as the prosthetic heart valve is radially compressed with the crimping device.

In some embodiments, the distal end of each arm can include a sloped surface configured to interface with the crimping device such that, upon actuation of the crimping device, the crimping device can exert a force to the sloped surface and urge the corresponding arm proximally relative to the valve alignment portion.

Further, certain embodiments of the disclosure concern a positioning device for positioning a prosthetic heart valve on a delivery apparatus. The positioning device can include a body and one or more coupling members that are mateable with one or more complementary coupling members of a prosthetic heart valve holder device. The body can include an interior surface defining an axially extending passage that is sized to form an interference fit with a shaft of the delivery apparatus.

In some embodiments, the inner surface of the body can include a row of a plurality of circumferentially oriented grooves extending from a proximal end of the body to a distal end of the body such that a sterilization gas can permeate into the passage through the plurality of grooves when the body is coupled to the shaft.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, which proceeds with reference to the accompanying figures.

BRIEF DESCRIPTION OF THE DRAWINGS

FIG. 3A shows a side elevation view of a delivery apparatus, according to one embodiment.

FIG. 3B shows an enlarged view of the distal end portion of the delivery apparatus of FIG. 3A.

FIG. 16A is a side perspective view of a valve retaining member, according to another embodiment.

FIG. 16B is a front perspective view of an alternative embodiment of a holder device including a plurality of valve retaining members as depicted in FIG. 16A.

DETAILED DESCRIPTION

Figure 1:
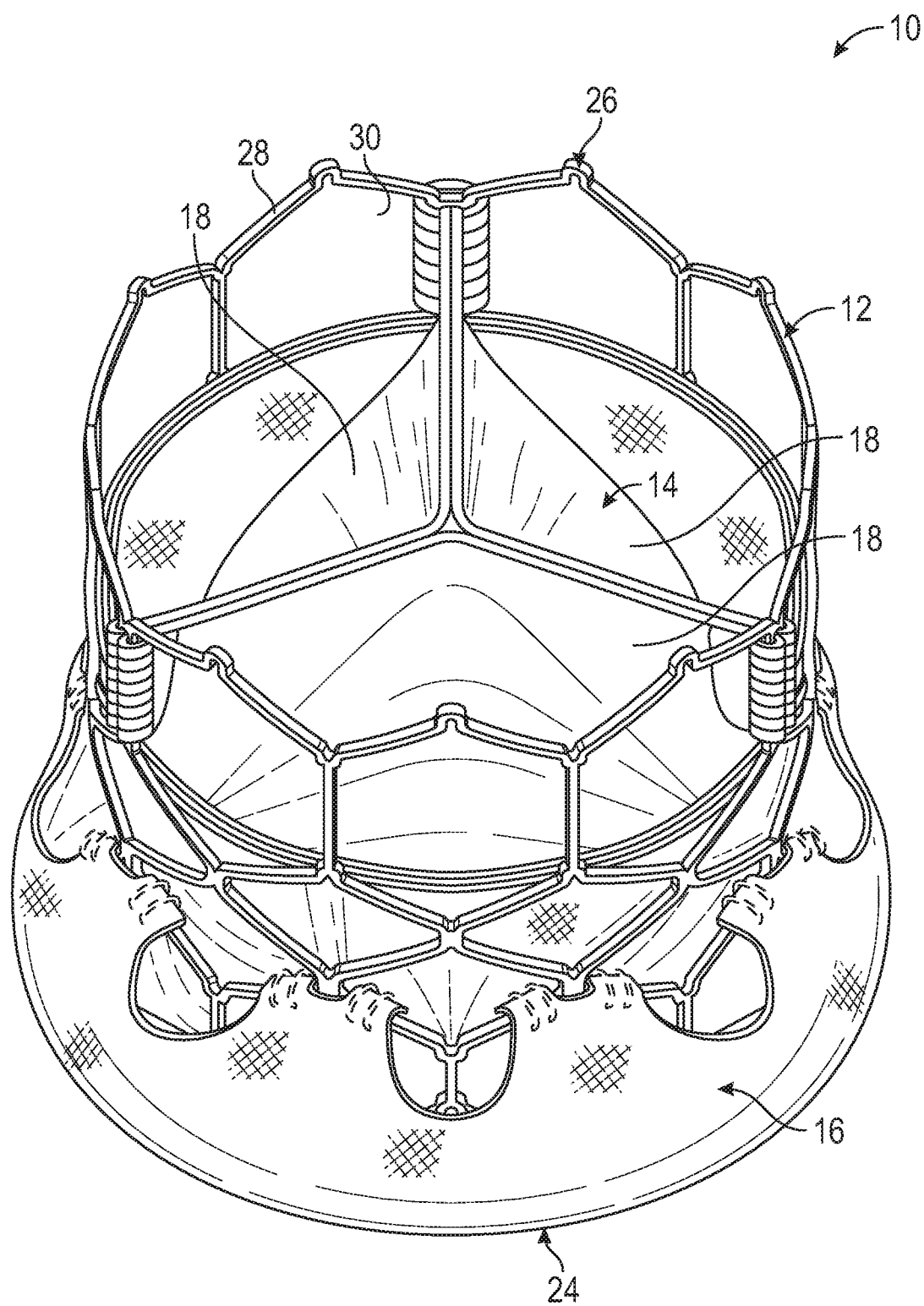
FIG. 1 shows a perspective view of an exemplary prosthetic heart valve.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

It should be noted at the outset that although prosthetic heart valves are used as exemplary collapsible prosthetic devices, the disclosed technology can be used with various other types of collapsible prosthetic devices such as stents and/or valve repair devices.

For various reasons, a prosthetic heart valve can be stored and shipped in its expanded state. When a prosthetic heart valve for a transvascular implantation procedure, the prosthetic heart valve can be crimped onto a designated landing zone (also referred to as a "crimping area" or "valve mounting portion") of the delivery apparatus. In many instances, high precision and accuracy are required during crimping.

Precise and accurate alignment of the crimped prosthetic heart valve with the designated landing zone can be challenging, for example, because a prosthetic heart valve may elongate longitudinally during the crimping procedure. Moreover, the crimping area can be obscured from the user's view by the crimping jaws of the crimping device, thus making it difficult to see location of the prosthetic heart valve during the crimping procedure.

Although occasionally a prosthetic heart valve may be crimped in a sub-optimal position, adjustment may be made by sliding it into place after it is crimped. Such adjustment is not recommended, due to possible damage to the leaflets of the prosthetic heart valve. This can even necessitate discarding the entire delivery system and the prosthetic heart valve, which is both expensive and wasteful.

In addition, particular care must be taken to ensure the prosthetic heart valve is oriented correctly on the delivery apparatus. For example, for a transfemoral delivery approach, the prosthetic valve is mounted on the delivery apparatus in a first orientation (the inlet of the prosthetic valve is mounted distally relative to the outlet for implanting at the aortic position), whereas for a transventricular approach, the prosthetic heart valve is mounted on the delivery apparatus in a second orientation (the outlet of the prosthetic valve is mounted distally relative to the inlet for implanting at the aortic position).

As a result, the crimping procedure usually needs to be performed by a highly trained clinical specialist and is time consuming. Thus, there is a need for improved devices and methods for faster, easier, and more accurate crimping of prosthetic heart valves.

Disclosed herein are various devices and methods that can, for example, make crimping a prosthetic heart valve more accurate, easier, quicker, and/or more repeatable. The disclosed devices and methods can, among other things, reduce the level of skill and/or training required for personnel to perform the crimping procedure. This in turn can reduce costs associated with such procedures.

Prosthetic Heart Valve

FIG. 1 shows an exemplary prosthetic heart valve 10. The valve 10 can have several main components: a stent or frame 12, a valvular structure 14, and a skirt assembly 16.

The frame 12 can have an annular shape and defines an inlet end 24 and an outlet end 26 of the prosthetic heart valve. The valvular structure 14 can be configured to permit blood to flow through the prosthetic heart valve 10 in a direction from the inlet end 24 to the outlet end 26 of the prosthetic heart valve and to block the flow of blood through the prosthetic heart valve in a direction from the outlet end 26 to the inlet end 24. The frame 12 can include a plurality of struts 28 that collectively define a plurality of open cells 30 of the frame 12. The valvular structure 14 can comprise one or more leaflets 18 (three in the illustrated embodiment), which can be made from natural tissue (e.g., pericardial tissue) and/or any of various synthetic materials.

The frame 12 can be made of any of various suitable plastically-expandable materials (e.g., stainless steel, cobalt-chromium alloys, etc.) or self-expanding materials (e.g., Nitinol) as known in the art. When constructed of a plastically-expandable material, the frame 12 (and thus the valve 10) can be crimped to a radially compressed configuration on a delivery apparatus and then expanded inside a patient by an inflatable balloon or another suitable expansion mechanism. When constructed of a self-expandable material, the frame 12 (and thus the valve 10) can be crimped to a radially compressed configuration and restrained in the compressed configuration by insertion into a sheath or equivalent mechanism of a delivery apparatus. Once inside the body, the valve can be advanced from the delivery sheath, which allows the valve to expand to its functional size.

The prosthetic heart valve 10 can be adapted to be implanted in the native aortic annulus and/or other native annuluses of the heart. Additional details regarding prosthetic heart valves can be found, for example, in U.S. Pat. Nos. 9,393,110, 8,449,599, 7,999,394, 7,510,575, U.S. Patent Application Publication No. 2016/0317301, and U.S. patent application Ser. No. 15/664,430 (filed Jul. 31, 2017), all of which are incorporated by reference herein.

Mounting Assembly

Figure 2:
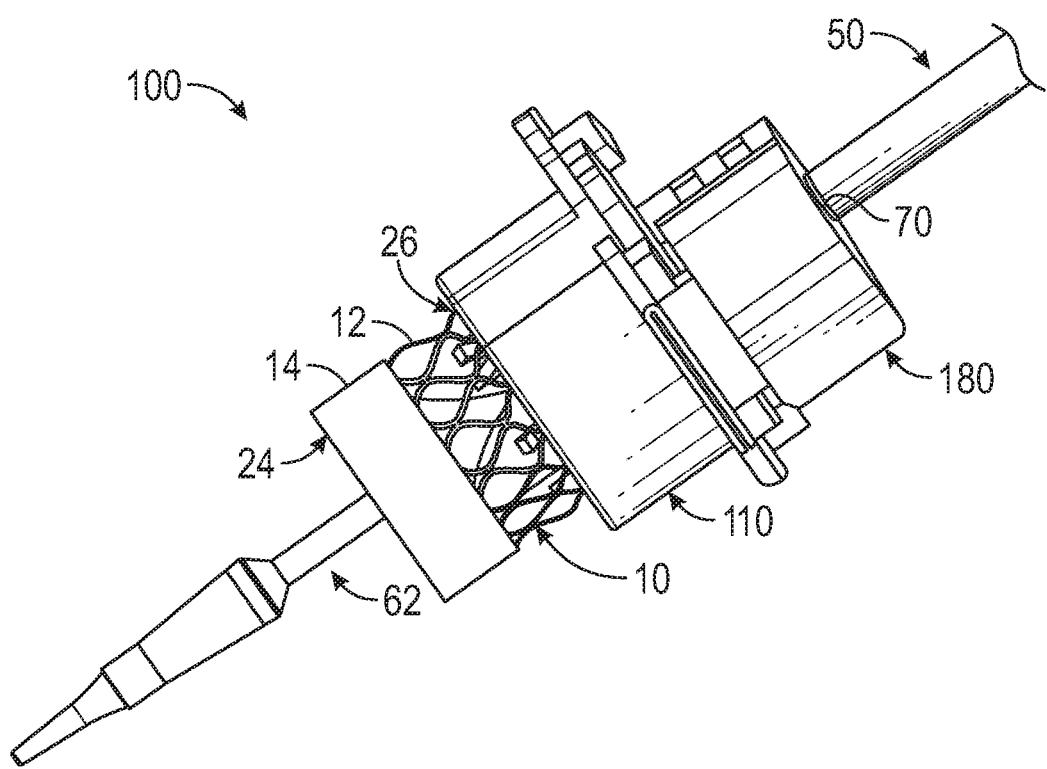
FIG. 2 shows a perspective view of a positioning and holder device assembly mounted on a delivery apparatus, according to one embodiment.

As shown in FIG. 2, the prosthetic heart valve 10 can be easily and accurately mounted to a delivery apparatus 50 using an exemplary mounting assembly 100. The mounting assembly 100 can comprise a positioning device 180 (also referred to as an alignment clip) that can be releasably mounted on or coupled to the delivery apparatus 50. The mounting assembly 100 can further comprise a holder device 110 that can be releasably coupled to the positioning device 180. In addition, the prosthetic heart valve 10 can be releasably coupled to the holder device 110, which holds the prosthetic heart valve at a predetermined position and in a predetermined orientation relative to the delivery apparatus for crimping the prosthetic valve onto the delivery apparatus 50 when the holder device is coupled to the positioning device 180, as further described below.

Figure 4A:
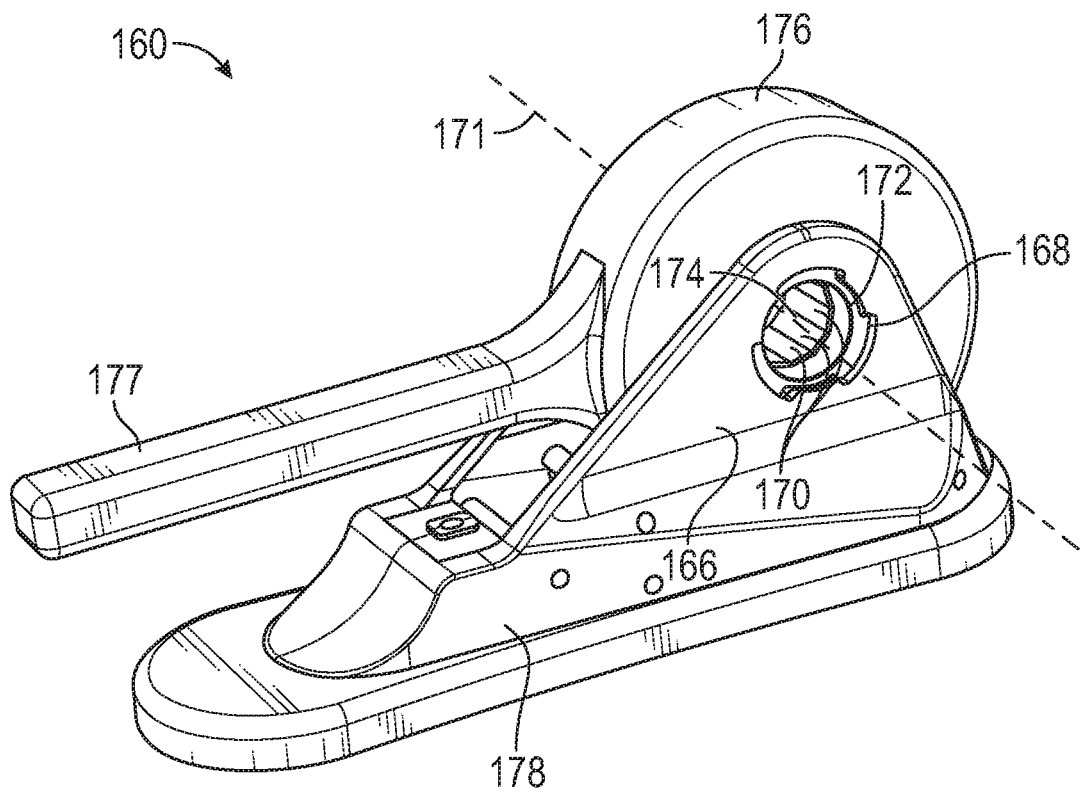
FIG. 4A shows a perspective view of a crimping device, according to one embodiment.

As described more fully below, the mounting assembly 100 can further comprise a crimping device, such as the crimping device 160 (FIG. 4A). The holder device 110 can be releasably coupled to the crimping device 160, and actuation of the crimping device can crimp the prosthetic heart valve 10 onto the delivery apparatus 50.

Figure 5A:
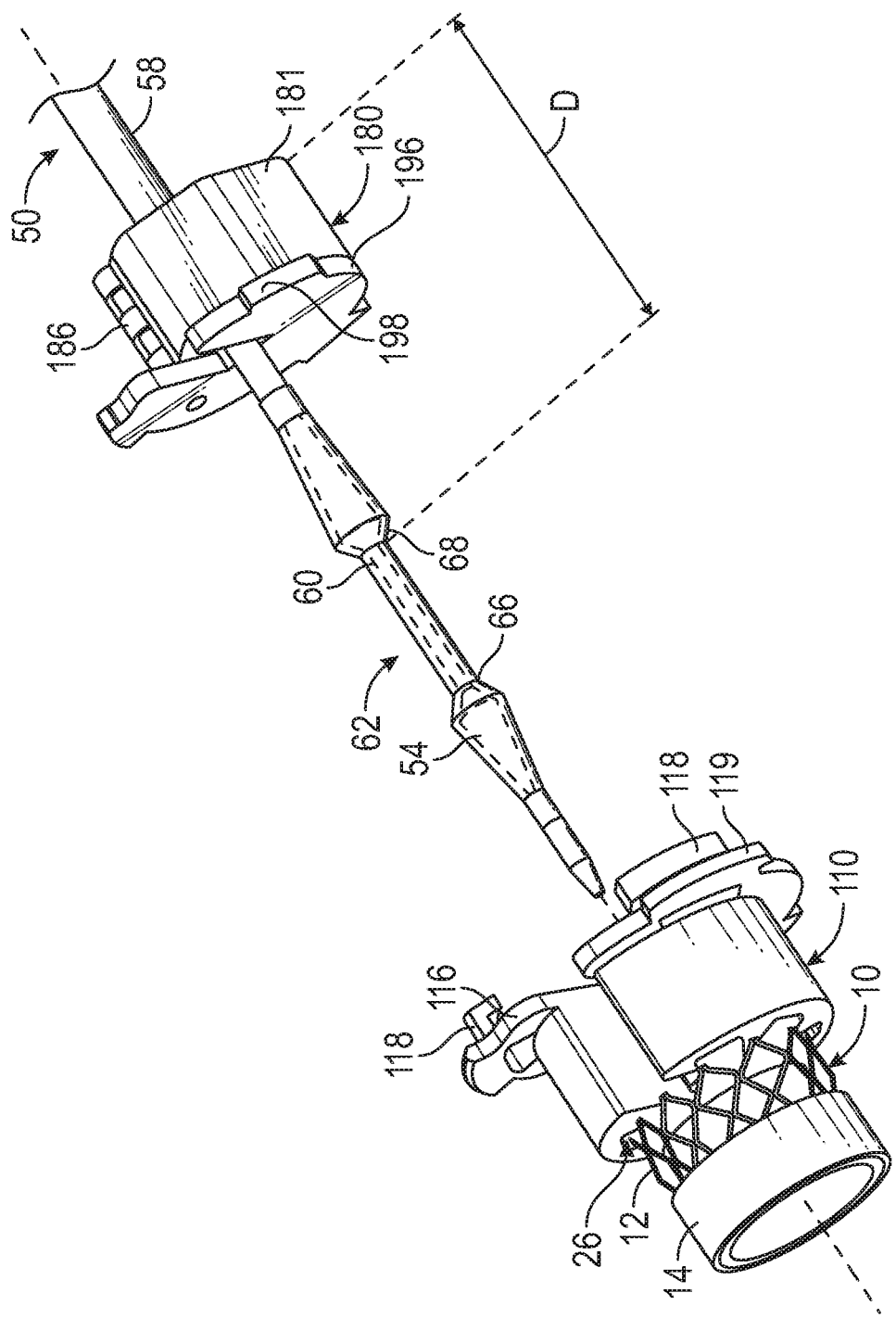
FIG. 5A is a perspective view showing a positioning device mounted at a predetermined location of the delivery apparatus and a holder device with a prosthetic valve being placed on the delivery apparatus.

Referring to FIGS. 2 and 5A, the outflow end 26 of the prosthetic heart valve 10 can be coupled to or supported by the holder device 110. In other embodiments, the inflow end 24 of the prosthetic heart valve 10 can be coupled to or supported by the holder device 110. It should be understood that the orientation of the prosthetic heart valve 10 will depend on the delivery technique used to implant the prosthetic heart valve. FIG. 2 shows the holder device 110 holding the outflow end 26 of the prosthetic valve positioned proximally relative to the inflow end 24 for delivering the prosthetic valve to the native aortic valve in a transfemoral delivery approach. Alternatively, the holder device 110 can hold the inflow end 24 of the prosthetic valve proximally relative to the outflow end 26 for delivering the prosthetic valve to the native aortic valve in a transventricular delivery approach.

Coupling the prosthetic heart valve 10 to the holder device 110 can, for example, occur as part of the manufacturing and/or packaging processes. Also as part of the manufacturing and/or packaging processes, the pre-coupled/pre-assembled prosthetic heart valve 10 and holder device 110 can be packaged with a delivery apparatus that corresponds to the orientation in which the prosthetic heart valve 10 is coupled to the holder device 110 (e.g., a transfemoral delivery apparatus is packaged with the prosthetic valve when prosthetic heart valve is coupled to the holder device in the transfemoral orientation shown in FIG. 2). Hence, matching the orientation of prosthetic heart valve and the delivery apparatus can, for example, reduce or eliminate the potential procedural error of mounting the prosthetic heart valve 10 in the reverse, and thus incorrect, orientation relative to the delivery apparatus (e.g., mounting a transfemorally oriented prosthetic heart valve on a transventricular delivery apparatus, or vice versa).

In particular embodiments, the positioning device 180 can be pre-mounted on the delivery apparatus at a predetermined location such that when holder device 110 is coupled to the positioning device 180 (with the prosthetic heart valve 10 pre-coupled to the holder device 110) by the end user, the prosthetic heart valve 10 is precisely aligned with respect to a valve mounting portion of the delivery apparatus for subsequent crimping. Thus, in this manner, the assembly comprised of the holder device 110 and the prosthetic heart valve 10 can be separately stored from the delivery apparatus (such as when the prosthetic heart valve is stored in a preservative solution), yet the end user can easily connect the holder device 110 to the positioning device 110 in the operating theater, which automatically positions the prosthetic heart valve at the desired location relative to the delivery apparatus for subsequent crimping just prior to implantation, thereby reducing procedure time and the potential for procedural error.

In particular embodiments, the pre-coupled/pre-assembled prosthetic heart valve 10 and holder device 110 can be pre-coupled to the positioning device 180, which in turn is pre-mounted on a delivery apparatus in the final orientation and packaged together in a sterile package for shipment to the end user. In this manner, there is no need for the end user (e.g., a physician) to couple the holder device 110 to the positing device 180 or to mount the positioning device 180 on the delivery apparatus, thus further reducing procedure time. Such embodiments can be advantageous where the prosthetic heart valve need not be stored separately from the delivery apparatus in a preservative solution. For example, a prosthetic heart valve having so-called dry tissue leaflets are treated during the manufacturing process such that the prosthetic heart valve can be stored in a dry state (not immersed in a preservative solution).

In some embodiments, the holder device 110 and the positioning device 180 are not separable components and instead comprise a single holder and positioning device that is configured to be mounted to a delivery apparatus and releasably hold a prosthetic heart valve 10. Such embodiments can be used, for example, where the prosthetic heart valve can be stored in a dry state. The holder and positioning device can be pre-mounted on the delivery apparatus and the prosthetic heart valve can be pre-coupled to the holder and positioning device and all three components can be contained in the same sterile package for shipping and storage. The holder and positioning device can include a holder portion configured to hold a prosthetic valve and a positioning portion configured to be mounted on the delivery apparatus.

As used herein, the terms "pre-coupled" or "pre-assembled" or "pre-mounted" means that two components are coupled or assembled together or one component is mounted on the other by the manufacturer prior to being placed in packaging and shipped from the manufacturer to a distributor or end user (e.g., a hospital).

To further aid in accurately pairing the prosthetic heart valve and the delivery apparatus, one or more of the components can be color coded with colored indicia or other types of visual indicia representative of the delivery technique to be used for implanting the prosthetic valve. For example, a holder device 110 can be a first color (e.g., red) when a prosthetic heart valve is coupled thereto for transfemoral delivery, and a delivery apparatus and/or a positioning device configured for transfemoral delivery can also be the same first color. As another example, a holder device 110 can be a second color (e.g., green) when a prosthetic heart valve is coupled thereto for transventricular delivery, and the delivery apparatus and/or the positioning device configured for transventricular delivery can also be the same second color. In this manner, the color coding can help an assembler and/or a user select and/or ensure that the prosthetic heart valve and delivery apparatus are accurately paired.

Delivery Apparatus

FIGS. 3A and 3B shows the delivery apparatus 50, according to one embodiment. The delivery apparatus 50 can comprise a handle 52 and an outer shaft 58 extending distally therefrom. The delivery apparatus 50 can also comprise an inner shaft 60 extending distally from the handle 52 and coaxially through the outer shaft 58. The inner shaft 60 can be referred to as an implant catheter because a prosthetic heart valve can be mounted onto the inner shaft for delivery into a patient's body. In some embodiments, the inner shaft 60 can be movable relative to the outer shaft 58 (i.e., the inner shaft can be rotated and/or moved axially relative to the outer shaft, or vice versa).

The delivery apparatus 50 can further have a nose cone 64 coupled to the distal end portion of the inner shaft 60. The inner shaft 60 can have a valve mounting portion (or designated landing zone) 62 that is located adjacent and proximal to the nose cone 64. The valve mounting portion 62 can have a proximal end 68 and a distal end 66. The axial length L of the valve mounting portion 62 measured between the proximal end 68 and the distal end 66 can be approximately equal to the axial length of the prosthetic heart valve 10 when it is fully crimped onto the implant catheter 60. The delivery apparatus 50 can also have proximal and distal stops 74 and 76, respectively, mounted on the inner shaft 60, with the space between the proximal and distal stops defining the valve mounting portion. The proximal stop 74 can be mounted to the distal end portion 59 of the outer shaft and/or to the outer surface of the inner shaft 60. The distal stop 76 can be formed as the proximal end portion of the nose cone 64, although in other embodiments it may be separately formed and affixed to the nose cone and/or the outer surface of the inner shaft 60.

Although not shown, a guide wire can extend through a central lumen of the inner shaft 60 and an inner lumen of the nose cone 64, so that the delivery apparatus 50 can be advanced over the guide wire which is inserted into a patient's vasculature.

The handle 52 can be configured to position and/or manipulate the outer shaft 58. For example, the handle 52 can include an actuation mechanism (e.g., a rotatable knob) that is configured to cause the outer shaft 58 to rotate about and/or slide along its longitudinal axis relative to the inner shaft 60.

The distal part of the delivery apparatus 50 can include a steerable section 56 having sufficient flexibility so that it can pass through tortuous anatomy without sacrificing rigidness of the outer shaft 58. In addition, the delivery apparatus 50 can include one or more pull wires (not shown) configured to cause the steerable section 56 to curve in a given direction, or to straighten.

For example, a pull wire can extend through a lumen in the outer shaft 58. A distal end of the pull wire can be fixedly secured to the distal end portion 59 of the outer shaft 58. A proximal end of the pull wire can be operatively connected to a steering mechanism (e.g., such as the illustrated rotatable knob 78, a button, etc.) located on the handle 52. Actuating the steering mechanism can increase or decrease tension on the pull wire, which in turn can cause the steerable section 56 to bend or straighten.

In some embodiments, the terminal distal end 80 of the outer shaft 58 can be positioned to be proximal and immediately adjacent the proximal stop 74 so as to minimize the overall length of the relatively stiffer distal straight section of the delivery apparatus (which includes the valve mounting portion 62, the proximal and distal stops 74, 76, and the nose cone 64), thereby improving the tracking performance of the delivery apparatus 50. In some embodiments, the distal end of the pull wire can be secured to the outer shaft 58 at or slightly proximal of the terminal distal end 80 of the outer shaft to maximize the overall length of the steerable section 56.

The embodiment shown in FIGS. 3A and 3B has an inflatable balloon 54 mounted on the inner shaft 60, overlying the valve mounting portion 62. The proximal end portion 54p of the balloon 54 can extend over the proximal stop 74 and can be secured to the outer surface of the distal end portion 59 of the outer shaft 58. The distal end portion 54d of the balloon 54 can extend over the distal stop 76 and can be secured to the outer surface of the nose cone 64.

As depicted, the balloon 54 can have a proximal shoulder 67, a distal shoulder 65, and an intermediate portion 69 disposed between the shoulders 65, 67. The proximal shoulder 67 can be approximately aligned with the proximal end 68 of the valve mounting portion 62, and the distal shoulder 65 can be approximately aligned with the distal end 66 of the valve mounting portion 62. Both the proximal shoulder 67 and the distal shoulder 65 of the balloon 54 can taper radially outwardly from respective ends of the intermediate portion 69 to the proximal and distal stops 74, 76, respectively, so as to define a generally dog bone-shaped balloon 54. In this manner, the proximal and distal shoulders define ramped surfaces of the balloon.

The balloon 54 can be fluidly coupled to an inflation fluid conduit (not shown) of the outer shaft 58 which extends to a port 53 located on the handle 52 so that, when an inflation fluid (e.g., saline) is supplied to the balloon 54 via the port 53 and the inflation fluid conduit, the balloon 54 can be inflated from a collapsed configuration to an expanded configuration.

In some embodiments, a prosthetic heart valve 10 can be crimped on the balloon 54 which overlies the valve mounting portion 62. Thus, at the implantation site, the balloon 54 can be inflated to expand the prosthetic heart valve 10 to its fully functional size. The ramped shoulders 67 and 65 can, for example, facilitate smooth expansion of the prosthetic heart valve 10 and maintain the positioning of the prosthetic heart valve relative to the balloon 54 during expansion. The ramped shoulders can also facilitate easier retrieval of the balloon 54 after the implantation.

In other embodiments (not shown), a self-expanding prosthetic heart valve can be crimped and inserted into a sheath of a delivery apparatus. After placement in the body, the sheath can be withdrawn and the prosthetic heart valve can expand inside the body.

Additional details regarding delivery apparatuses can be found, for example, in U.S. Pat. No. 9,339,384 and U.S. Patent Application Publication No. 2017/0065415, both of which are incorporated by reference herein.

Crimping Device

FIG. 4A shows a crimping device 160, according to an exemplary embodiment. The crimping device 160 can have a window or opening 172 exposing a plurality of jaws 170, which are arranged around a central axis 171 of the jaws 170. The jaws 170 can define a variable-sized crimping aperture 174 between their inner ends. The jaws 170 can be located within a rotating portion comprising a housing 176 and operatively connected to an actuator in the form of a lever or handle 177 connected to and extending from the housing 176.

The crimping device 160 can further include a frame 178 which can act as a stand or base. The crimping device 160 can include a coupling mechanism that is configured to releasably couple to the holder device 110. For example, in the embodiment depicted in FIG. 4A, a proximal or front surface 166 of the frame 178 can have one or more catches 168 (e.g., three in the illustrated embodiment) which are configured to matingly engage with one or more corresponding tabs of the holder device 110, as described more fully below. As shown, the catches 168 can protrude radially outwardly relative to the window 172. The catches 168 can also be circumferentially distributed around the window 172.

FIG. 4A shows the crimping aperture 174 in an "open" position, with the jaws 170 moved to their radially outward positions such that the aperture 174 has a relatively large diameter. In the "open" position, an expanded annular implant (e.g., the prosthetic heart valve 10) can be inserted into the crimping aperture 174.

Figure 4B:
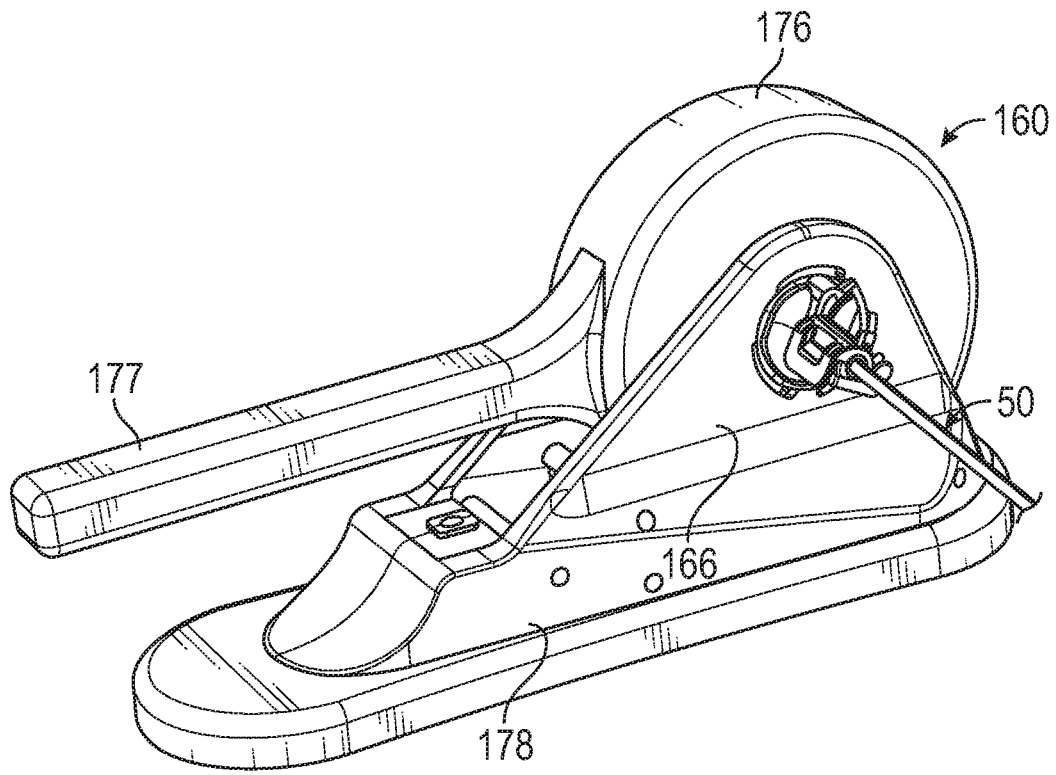
FIG. 4B shows a prosthetic valve and the distal end portion of a delivery apparatus inserted into a crimping aperture of the crimping device of FIG. 4A.

FIG. 4B shows the prosthetic heart valve 10 and the valve mounting portion 62 of the delivery apparatus 50 inserted into the crimping aperture 174. Actuating the crimping device 160, e.g., by pressing the lever 177 downwardly, moves the crimping aperture 174 from the "open" to a "closed" or constricted position. When moved to the closed position by the lever 177, the jaws 170 move radially inwardly toward each other so as to decrease the size of the crimping aperture 174 and compress the prosthetic heart valve onto the valve mounting portion 62 of the delivery apparatus 50.

Exemplary embodiments of crimping devices and the associated crimping methods are further described in U.S. Patent Application Publication Nos. 2015/0336150, 2015/0190225, 2013/0030418, and U.S. Pat. No. 7,993,394, the disclosures of which are incorporated by reference herein.

Mounting Process

FIG. 5A-5D illustrate a method of crimping the prosthetic heart valve 10 on the delivery apparatus 50, according to one exemplary embodiment. The prosthetic heart valve 10 is shown in an expanded configuration in FIGS. 5A-B, and in a compressed configuration in FIG. 5D. Generally, the prosthetic heart valve 10 in the compressed configuration has a longer axial dimension and a smaller radial cross-sectional dimension than in the expanded configuration.

As shown in FIG. 5A, the prosthetic heart valve 10 can be coupled to the holder device 110 to form a valve and holder device assembly. The positioning device 180 can be coupled to the outer shaft 58 of the delivery apparatus 50 at a predetermined location. For example, a proximal end of the positioning device 180 can be aligned with a marker 70 (FIG. 5B) on the outer shaft 58 and secured to the outer shaft 58 against inadvertent movement (rotational and axial movement) relative to the outer shaft. The marker 70 can be spaced relative to the valve mounting portion 62 of the implant catheter 60. The axial distance D between the marker 70 and the proximal end 68 of the valve mounting portion 62 can be predetermined to align the prosthetic heart valve with the valve mounting portion 62, as further detailed below.

Figure 5B:
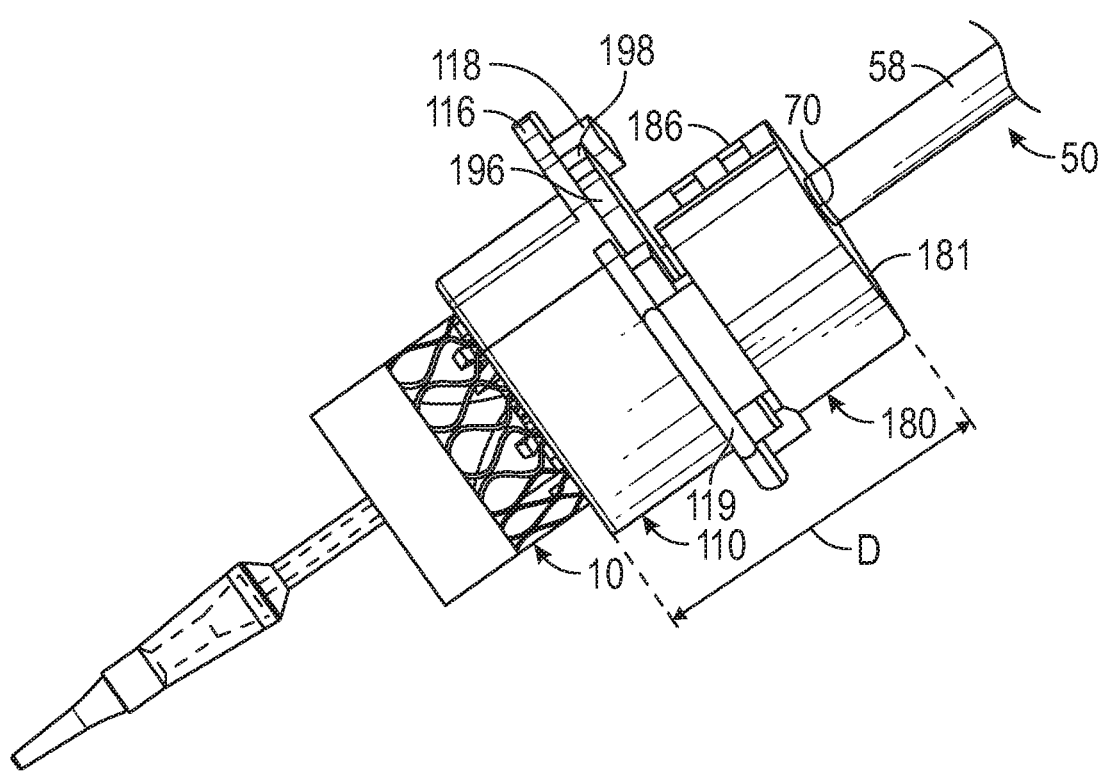
FIG. 5B is a perspective view similar to FIG. 5A, after the holder device is coupled to the positioning device.

As shown in FIG. 5B, the valve and holder device assembly can be positioned over the delivery apparatus 50 and coupled to the positioning device 180. The positioning of the positioning device 180 relative to the delivery catheter 50 can be configured so as to align the prosthetic heart valve 10 relative to the delivery apparatus 50. For example, the proximal end portion of the holder device 110 can be releasably coupled to a distal end of the positioning device 180. Because the location of the positioning device 180 on the delivery apparatus 50 is predetermined, the location of the prosthetic heart valve 10 (which is coupled to the holder device 110) on the delivery apparatus 50 can also be predetermined. Specifically, when the holder device 110 is coupled to the positioning device 180, the proximal end of the prosthetic heart valve 10 can be aligned with the proximal end 68 of the valve mounting portion 62.

Figure 5C:
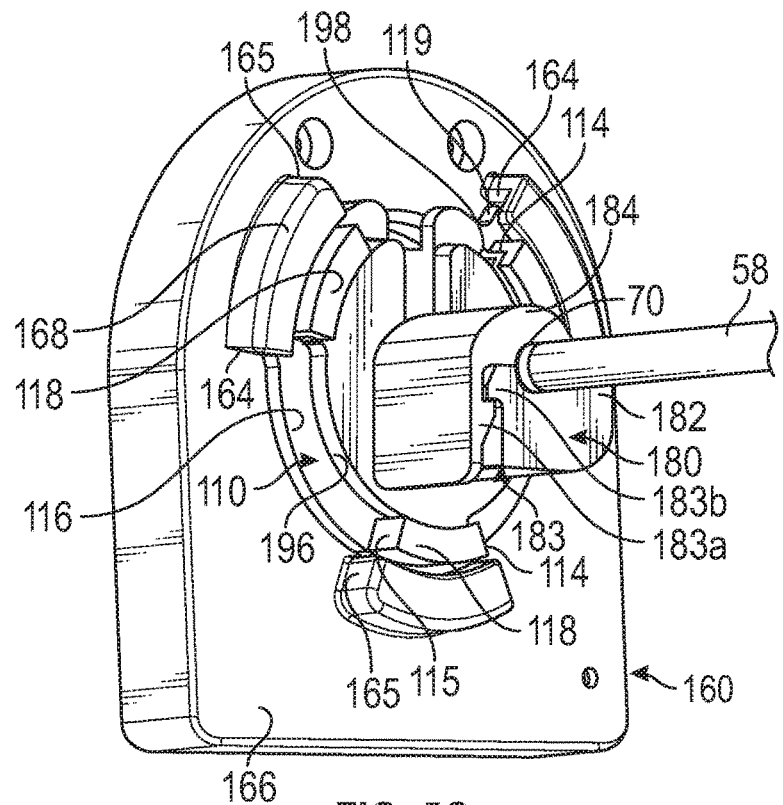
FIG. 5C is a perspective view showing the holder device coupled to the front face of the crimping device.

With the positioning device, the holder device and the prosthetic valve mounted on the delivery apparatus as shown in FIG. 5B, the prosthetic heart valve 10 and the delivery apparatus 50 can then be inserted into the crimping device 160, as shown in FIG. 5C. The holder device 110 (together with the positioning device 180) can be coupled to the crimping device 160, so as to align the prosthetic heart valve 10 relative to the crimping jaws 170 of the crimping device 160.

When so coupled to the crimping device, the engagement of the holder device 110 with the catches 168 on the crimping device is effective to place the prosthetic valve 10 at a desired location within the crimping aperture 174 and retain the prosthetic heart valve and the delivery apparatus against movement relative to the crimping device. As noted above, the positioning device 180 retains the holding device 110 and the prosthetic valve 110 at a fixed location relative to the delivery apparatus. Thus, when the holding device is coupled to the crimping device as shown in FIG. 5C, the prosthetic valve 10 is held at a desired location along the delivery apparatus within the crimping device for subsequent crimping of the prosthetic valve at the valve mounting portion 62. Advantageously, the user need not have to manually position the prosthetic valve relative to the crimping jaws and the valve mounting portion 62 and hold those positions while operating the crimping device.

Figure 5D:
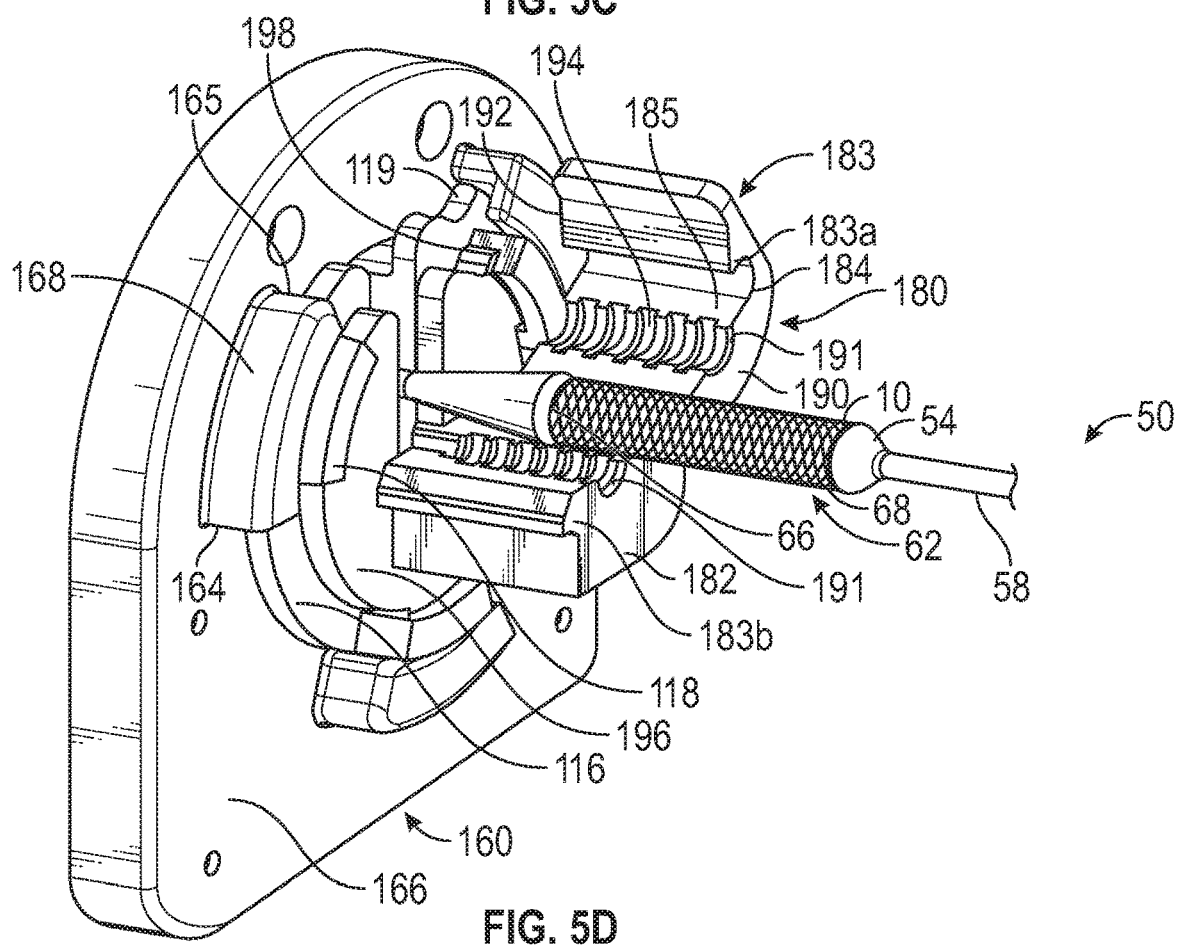
FIG. 5D is a perspective view showing the removal of the delivery apparatus, together with the prosthetic heart valve crimped thereon, from the holder device and the crimping device.

The crimping device 160 can then be used to crimp the prosthetic heart valve 10 onto the delivery apparatus 50, as shown in FIG. 5D. As described more fully below, actuating the crimping device 160 can release the prosthetic heart valve 10 from the holder device 110. In addition, actuating the crimping device 160 can radially compress the prosthetic heart valve 10 from the expanded configuration to the compressed configuration. Because the crimped prosthetic heart valve 10 has a reduced radial cross-sectional dimension and is decoupled from the holder device 110, the delivery apparatus 50, together with the prosthetic heart valve 10 crimped thereon, can then be removed from the mounting assembly 100.

Figure 6:
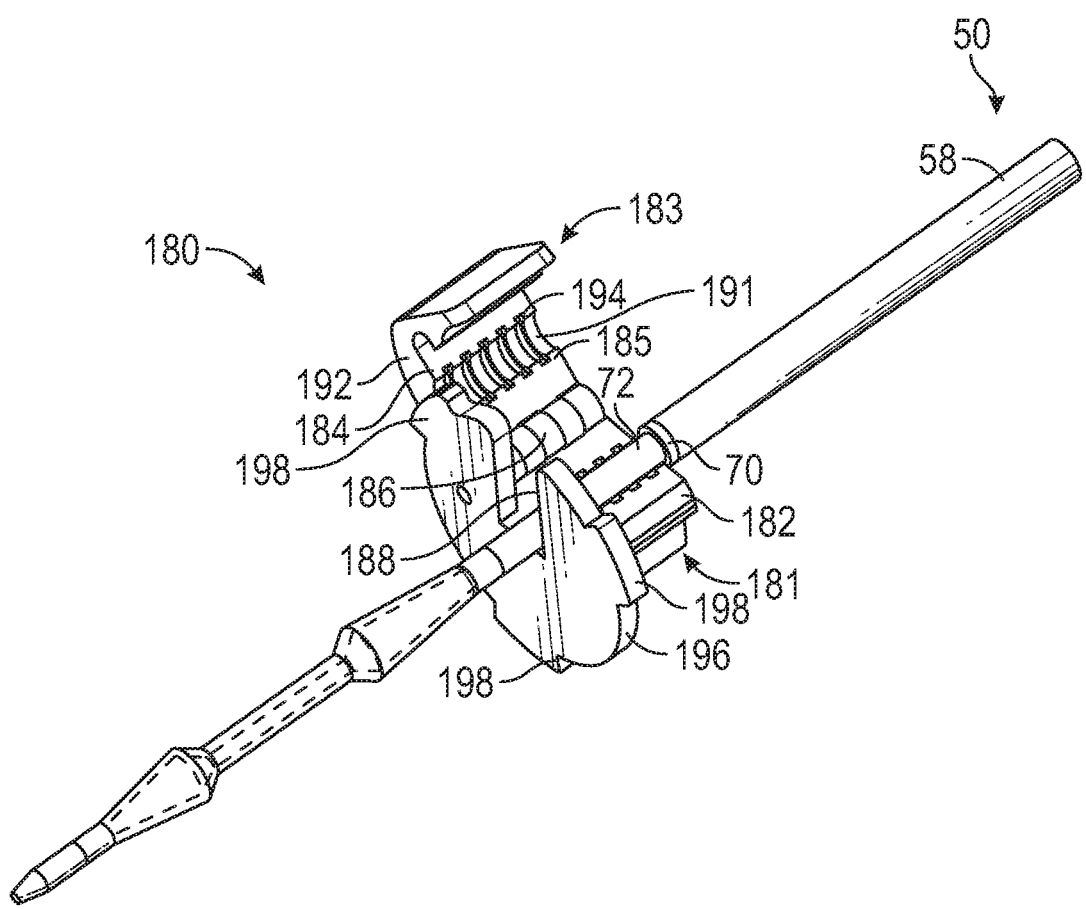
FIG. 6 is a perspective view showing the positioning device being removed from the delivery apparatus.

Additional details of these components and various methods for using the components are further described below.
Positioning Device FIG. 6 shows one exemplary embodiment of the positioning device 180. As shown, the positioning device 180 in the illustrated embodiment can include a body 181 having a clam-shell configuration comprising a first portion 182 and a second portion 184 that are hingedly connected to each other by a hinge member 186. The first and second portions 182, 184 can be pivoted relative to each other between an open position (shown in FIG. 6) and a closed position (FIG. 5C). The positioning device 180 can also include a fastening or latching mechanism, shown generally at 183, configured to retain the body 181 in the closed position while mounted on the delivery apparatus 50.

The body 181 can have an interior surface 185 defining a central passage or lumen 188 that receives the outer shaft of the the delivery apparatus 50. The central passage 188 can be sized to form an interference or frictional fit with a segment 72 of the outer shaft 58 that is adjacent and distal to the marker 70. In particular embodiments, when the body 181 is in a closed position around the segment 72, the interference fit with the segment 72 is sufficient to hold the positioning device stationary against rotational and axial movement relative to the shaft during normal use and handling.

It should be noted that the marker 70 can be an annular shoulder or ridge or can be a line or another type of visual indicia formed or printed on the shaft 58. In the illustrated embodiment, the segment 72 can have a reduced outer diameter compared to the portion of the shaft 58 proximal to the segment 72 so as to define an annular shoulder 70 that can abut an adjacent surface of the positioning device 180 and prevent axial movement of the positioning device in the proximal direction along the outer shaft 58.

In the closed configuration (e.g., FIGS. 2 and 5A-C), the first and second portions 182 and 184 are held in the closed position by the fastening mechanism 183 such that the segment 72 of the outer shaft 58 is completely surrounded by the body 181.

In the depicted embodiment, the fastening mechanism 183 includes an outwardly extending protrusion 183b (FIG. 5D) located on the inner surface of the first portion 182 opposite the hinge member 186, and an inwardly extending protrusion 183a (FIG. 5D) located on the inner surface of the second portion 184 opposite the hinge member 186. The protrusions 183a, 183b can be complementarily shaped and sized to form a snap-fit connection with each other. Thus, the first and second portions 182, 184 can be placed in the closed configuration by urging the protrusion 183a against the protrusion 183b until the protrusion 183a slides over the protrusion 183b and engages an adjacent surface thereof, as shown in FIG. 5C. When closing the positing device, the second portion 184 can deflect or deform slightly to allow the protrusion 183a to pass over the protrusion 183b, and then reverts back to its original shape to hold the second portion 184 in the closed position relative to the first portion 182. To open the positioning device 180, the second portion 184 can be pried away from the first portion 182 to allow the protrusion 183a to pass back over the protrusion 183b as the second portion 184 is pivoted toward the open position. In alternative embodiments, various other types of fastening mechanisms can also be used to retain the first and second portions 182, 184 in the closed position, such as clips, hooks, locks, keys, claps, snaps, buttons, buckles, zippers, hook-and-loop fasteners, magnets, etc.

As further shown in FIG. 5D, the inner surface 185 of the body 181 can include one or more grooved paths 191 extending from a proximal end 190 of the body 181 to a distal end 192 of the body 181. Each grooved path 191 can have a plurality of axially spaced, circumferentially oriented grooves 194 formed on the interior surface 185. Although two grooved paths 191 are shown in FIGS. 5D and 6 (one on the inner surface of the first portion 182 and one on the inner surface of the second portion 184), it should be understood that the body 181 can have any number of grooved paths 191 that are circumferentially disposed on the inner surface 185. When the positioning device is closed, grooves on the first portion 182 can align with respective grooves on the second portion 184 such that each groove on the first portion 182 is paired with a respective groove on the second portion 184 to define a full groove that extends through 360 degrees along the inner surface 185 of the body 181.

Because the grooved paths 191 create a void space on the inner surface 185 and they extend through the body 181, a sterilization gas can permeate or flow into the central passage 188 through the grooved paths 191 even as the body 181 is coupled to the outer shaft 58 and in the closed position. Thus, both the inner surface 185 of the positioning device 180 and the outer surface of the outer shaft 58 extending therethrough can be sterilized by the sterilization gas when the positioning device 180 is coupled to the delivery apparatus 50. For example, after the prosthetic valve and the components of the mounting assembly are removed from their packaging by the end user and assembled on the delivery apparatus as shown in FIG. 5B (if any components are not already pre-assembled or pre-mounted), the prosthetic valve, the delivery apparatus 50, and the mounting assembly can be exposed to an ethylene oxide sterilization process (or another sterilization gas) if re-sterilization of any of these components is deemed necessary prior to implantation.

In alternative embodiments, one or more of the grooves 194 can be replaced by one or more slots that extend through the body 181 from the outer surface to the inner surface 185. In the closed configuration, the slots allow the sterilization gas to permeate or flow into the central passage 188 for sterilization.

In addition, the positioning device 180 can have a flange 196 connected to the first portion 182 adjacent the distal end 192 of the body 181. The flange 196 can have a larger radial diameter than the body 181. In certain embodiments, one or more tabs 198 can project radially outwardly from the outer edge of the flange 196. The flange 196 and/or tabs 198 can be used, for example, to couple the positioning device 180 to the holder device 110, as further discussed below.

Coupling Mechanisms

FIGS. 5A-5D further illustrate the manner in which the holder device 110 is coupled to the positioning device 180 and the holder device 110 is coupled to the crimping device 160.

For example, as shown in FIG. 5A, the proximal end of the holder device 110 can have a flange 116, which can be configured to be releasably coupled to the flange 196 of the positioning device 180. The flange 116 of the holder device 110 can be configured to be releasably coupled to the crimping device 160.

In certain embodiments, the flange 116 of the holder device 110 can have one or more catches 118 protruding axially outwardly from the proximal face of the flange 116. The catches 118 of the holder device can have interior recesses that are complementary to the one or more tabs 198 located on the flange 196 of the positioning device 180. In other words, the catches 118 of the holder device 110 can be are so sized, shaped, and positioned as to be capable of matingly engaging with the corresponding tabs 196 of the positioning device 180.

As best shown in FIG. 5C, each catch 118 can span an arc circumferentially, and have an open end 114 and a closed end 115 opposite the open end 114. The catches 118 can be sequentially arranged such that the open ends 114 and the close ends 115 of the catches 118 are juxtaposed circumferentially. Thus, coupling or uncoupling between the holder device 110 and the positioning device 180 can be accomplished by placing the flange 116 of the holder device 110 against the flange 196 of the positioning device 180 with the tabs 198 of the positioning device adjacent the open ends 114 of the catches 118 of the holding device, and then coaxially rotating the holder device 110 relative to the positioning device 180 to position the tabs 198 within respective catches 118.

For example, the holder device 110 can be coupled to the positioning device 180 by rotating the holder device 110 in one direction (e.g., clockwise) so that the tabs 198 can be inserted through the open ends 114 and into the interior recesses of the catches 118, while the insertion can be limited by the close ends 115 of the catches 118. Conversely, uncoupling between the holder device 110 and the positioning device 180 can be achieved by rotating the holder device 110 in the opposite direction (e.g., counter-clockwise) so that the tabs 198 can exit through the open ends 114.

In particular embodiments, the catches 118 can be sized and shaped to form an interference or frictional fit with the tabs 198 that is sufficient to hold the positioning device and the holding device together and prevent relative movement between the two components during normal use and handling. In some embodiments, the catches 118 and/or the tabs 198 can include additional features to help retain the positioning device and the holding device together, such as protrusions formed on one component and corresponding detents formed on another component that receive the protrusions.

In certain embodiments, the flange 116 of the holder device 110 can further include one or more tabs 119 protruding radially outwardly from the outer edge of the flange 116. As noted above, the front surface 166 of the crimping device 160 can have one or more catches 168 protruding axially outwardly from the proximal face of the crimping device 160. The catches 168 of the crimping device can have interior recesses that are complementary to the one or more tabs 119 located on the flange 116 of the holder device 110. In other words, the catches 168 of the crimping device 160 can be are so sized, shaped, and positioned as to be capable of matingly engaging with the corresponding tabs 119 of the holder device 110.

Figure 7A:
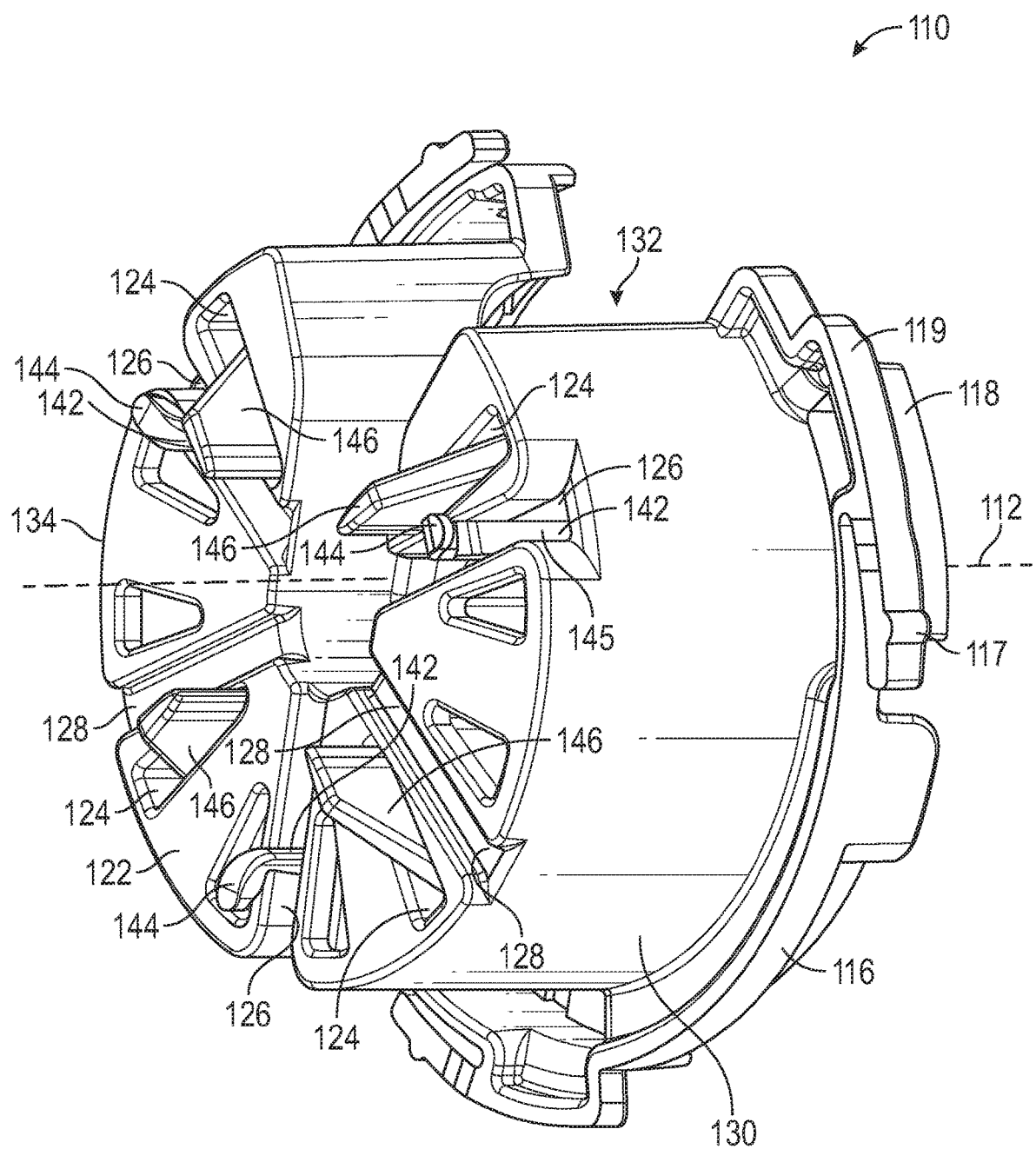
FIG. 7A shows a perspective view of a holder device, according to one embodiment.
Figure 7B:
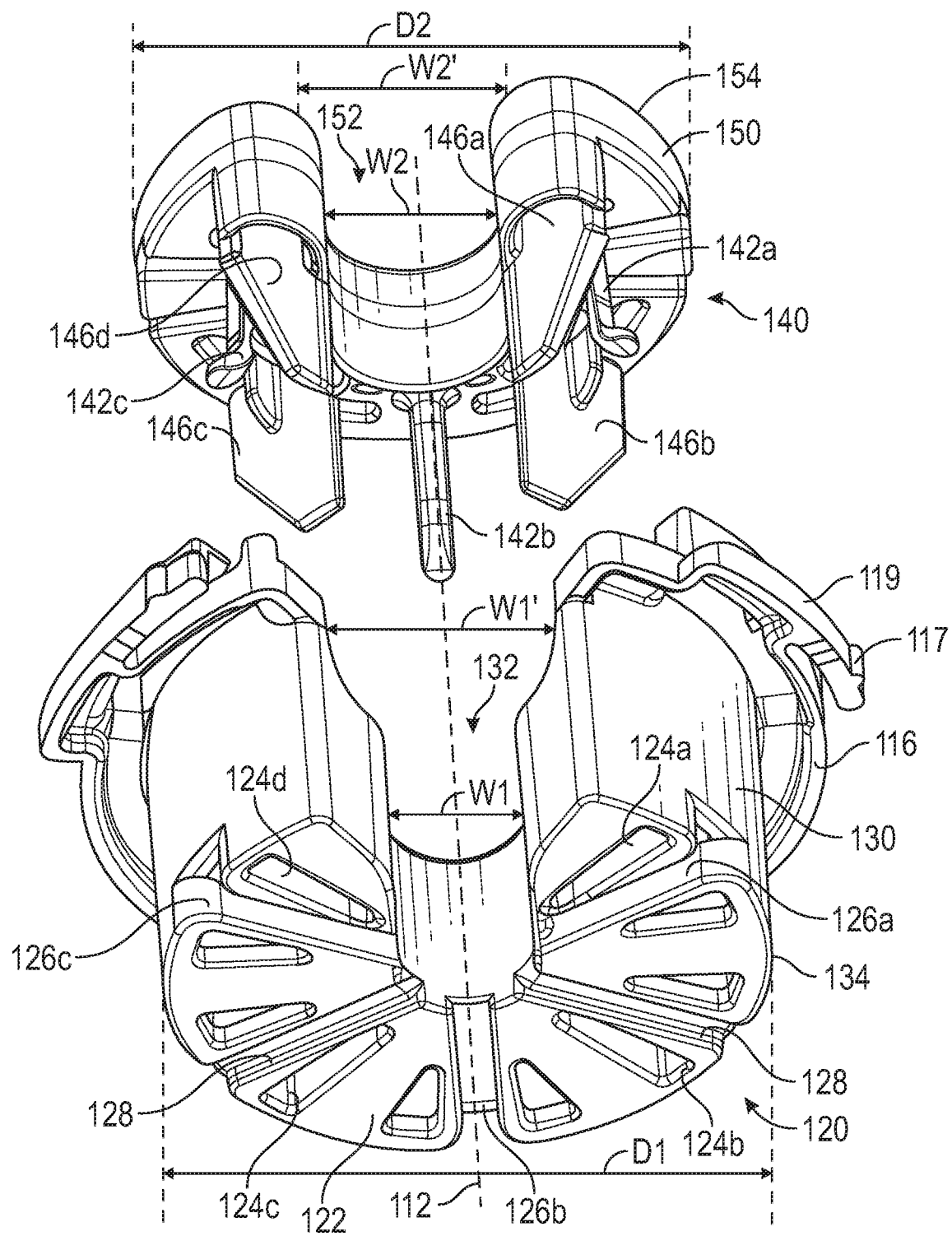
FIG. 7B shows a distal perspective, exploded view of the holder device of FIG. 7A.
Figure 7C:
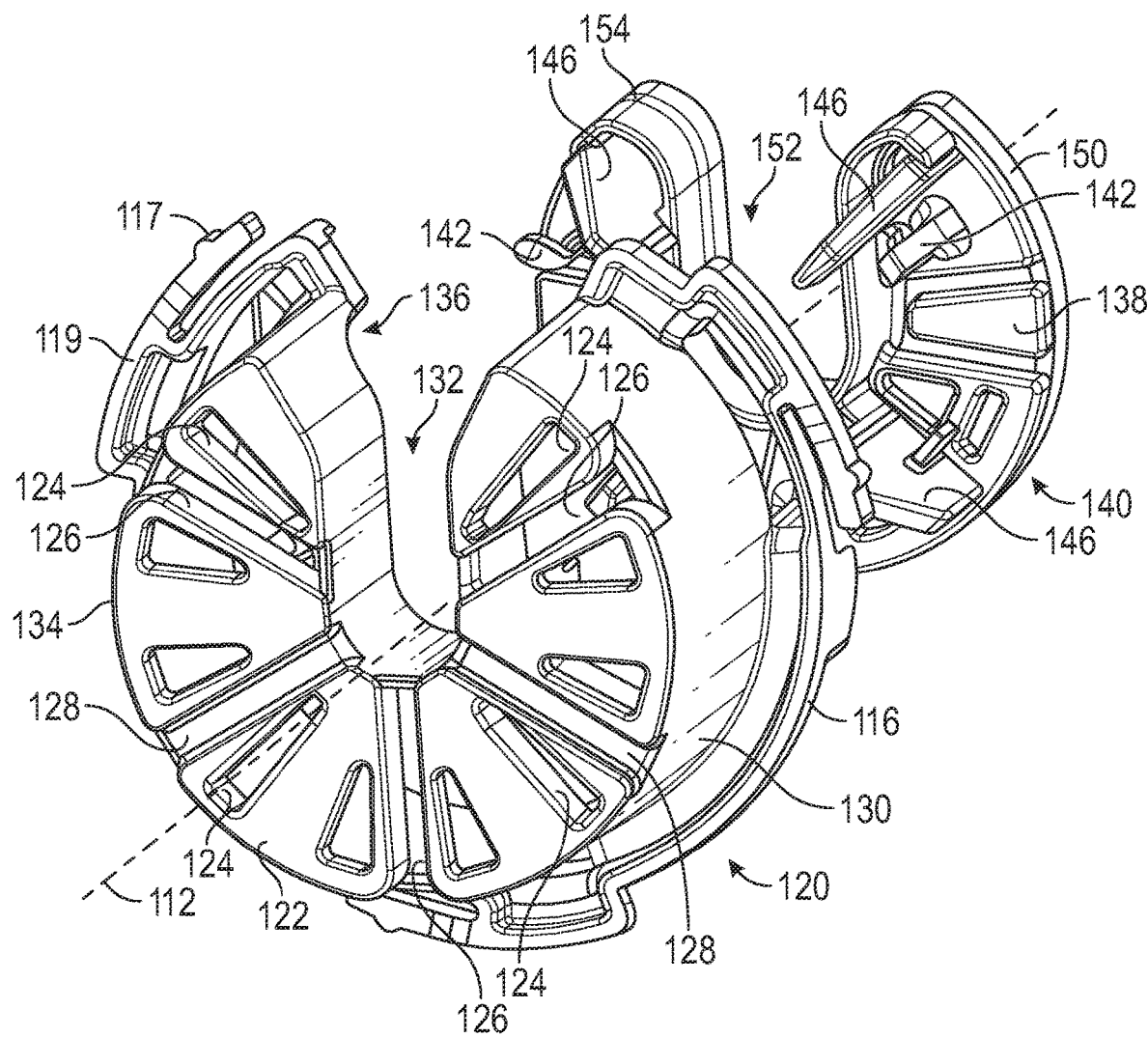
FIG. 7C shows a side perspective, exploded view of the holder device of FIG. 7A.

In some embodiments, each tab 119 can be a generally flat protrusion or extension of the flange 116 (e.g., FIGS. 5A-5D). In other embodiments, each tab 119 can comprise a cantilevered arm extending outwardly from the flange 116 (e.g., FIGS. 7A-7C). In addition, the tabs 119 and/or the catches 168 can include additional features to help retain the holder device 110 and the crimping device 160 together. For example, as illustrated in FIGS. 7A-7C, each tab 119 can comprise a small hump or protrusion 117 protruding outwardly from the cantilevered arm. The hump 117 can be configured to engage with a complimentary arranged detent (not shown) formed on the corresponding catch 168 of the crimping device to help retain the holder device 110 on the crimping device 160.

As best shown in FIGS. 5C and 5D, each catch 168 can span an arc circumferentially, and have an open end 164 and a closed end 165 opposite the open end 164. The catches 168 can be sequentially arranged such that the open ends 164 and the close ends 165 of the catches 168 are juxtaposed circumferentially. Thus, coupling or uncoupling between the crimping device 160 and the holder device 110 can be accomplished by placing the flange 166 of the holder device 110 against the front face 166 of the crimping device 160 with the tabs 119 adjacent the open ends 164 of the catches, and then coaxially rotating the holder device 110 relative to the crimping device 160.

For example, coupling between the holder device 110 and the crimping device 160 can be achieved by rotating the holder device 110 in one direction (e.g., clockwise) so that the tabs 119 can be inserted through the open ends 164 and into the interior recesses of the catches 168, while the insertion can be limited by the closed ends 165 of the catches 168. Conversely, uncoupling between the holder device 110 and the crimping device 160 can be achieved by rotating the holder device 110 in the opposite direction (e.g., counterclockwise) so that the tabs 119 can exit through the open ends 164.

In particular embodiments, the catches 168 can be sized and shaped to form an interference or frictional fit with the tabs 119 that is sufficient to hold the holder device 110 on the crimping device 160 and prevent relative movement between the two components during normal use and handling. In some embodiments, the catches 168 and/or the tabs 119 can include additional features to help retain the holding device on the crimping device 160, such as protrusions (e.g., protrusions 117) formed on one component and corresponding detents formed on another component that receive the protrusions.

In alternative embodiments, the holder device 110 may not have independent sets of catches 118 and tabs 119. For example, the holder device 110 can have one or more integrated coupling members (not shown), each of which can be configured to function both as a catch for a corresponding tab 198 on the positioning device 180 and as a tab for a corresponding catch 168 on the crimping device 160. In other words, the integrated coupling members on the holder device 110 can be configured to matingly engage the tabs 198 on the positioning device 180, as well as the catches 168 on the crimping device 160.

In alternative embodiments (not shown), the relative positions of the corresponding catches and tabs can be switched. For example, the positioning device 180 can have one or more catches that are capable to matingly engage with one or more tabs located on the holder device 110. Likewise, the crimping device 160 can have one more tabs that are capable to matingly engage with one or more catches located on the holder device 110.

Further, although FIGS. 5A-5D show that the complementarily configured tabs and catches are used to implement the coupling mechanisms between the holder device 110 and the positioning device 180, and between the crimping device 160 and the holder device 110, it should be understood that the depicted embodiments are merely for illustration purpose and not limiting. Other coupling mechanisms, such as clips, hooks, locks, keys, claps, snaps, buttons, buckles, zippers, hook and loop fasteners, magnets, etc., can also be employed, independently or in combination, to achieve coupling between the holder device 110 and the positioning device 180, and between the crimping device 160 and the holder device 110.

Holder Device

The holder device 110 is configured to hold the prosthetic heart valve 10 in the expanded configuration and to allow the prosthetic heart valve 10 to be inserted in the crimping device 160 so that the prosthetic heart valve 10 can be crimped onto the valve mounting portion 62 of the delivery apparatus 50.

In some embodiments, the holder device 110 can include one or more retaining members configured to secure the prosthetic heart valve 10 to the holder device 110 when the prosthetic heart valve 10 is in the expanded configuration and configured to release the prosthetic heart valve 10 from the holder device 110 when the prosthetic heart valve 10 is compressed with the crimping device from the expanded configuration to the compressed configuration.

Although embodiments of the holder device 110 described below include a valve alignment portion a valve retaining portion that are arranged in a specific structural configuration, it should be understood that other structural configurations are also possible to achieve the same function, and they are also within the scope of this disclosure. For example, in some embodiments, the valve alignment portion can be placed inside the valve retaining portion. In some embodiments, the valve alignment portion and the valve retaining portion can be an integrated piece and need not be separable from each other. In some embodiments, the retaining members can be located on any part of the holder device 110. In some embodiments, each of the retaining members can comprise an axially extending, telescoping beam that can be extending and retracted in an axial direction in a telescoping manner.

Referring now to FIGS. 7A-7C, the holder device 110 can include a first portion (also referred to as a "valve alignment portion") 120 and a second portion (also referred to as a "valve retaining portion") 140. As described below, the valve retaining portion 140 can be coaxially inserted into the valve alignment portion 120. Further, the valve retaining portion 140 can move proximally or distally relative to the valve alignment portion 120 along a central axis 112.

As shown in FIG. 7B, the valve retaining portion 140 can comprise a proximal plate 150 which can have a generally cylindrical shape, except for having a cavity 152 extending from an outer periphery 154 of the plate through the central axis 112. The cavity 152 can have a width that is narrower near the central axis 112 (e.g., inner width W2) and wider near the periphery (e.g., outer width W2').

The valve retaining portion 140 can further comprise a plurality of valve retaining members 142a, 142b, 142c, collectively referred to as retaining members 142 (three are shown). The valve retaining portion 140 can also include a plurality of extension arms 146a, 146b, 146c, 146d, collectively referred to as arms 146 (e.g., four are shown), which extend axially from the distal surface of the plate 150. As shown in FIG. 7A, each retaining member 142 can comprise a cantilevered beam 145 which extends axially from the distal surface of the plate 150 and a protrusion 144 which extends radially outwardly from a distal end portion of the beam 145. The retaining members 142 are configured to releasably hold the prosthetic valve 10 on the holder device 110, as further described below. The arms 146 are configured to engage the crimping jaws 170 of the crimping device 160, which produces movement of the valve retaining portion 140 relative to the valve alignment portion 120 during the crimping process, allowing the retaining members 142 to disengage from the prosthetic heart valve 10, as further described below.

The plurality of retaining members 142 can be circumferentially positioned relative to each other in a generally uniform pattern. For example, FIGS. 7A-7C shows three retaining members 142 spaced circumferentially apart from each other by about 120 degrees. Two of the retaining members 142a, 142c can be symmetrically located on opposite sides of the cavity 152, and the third retaining member 142b can be located diametrically opposite the cavity 152.

The plurality of arms 146 can be circumferentially positioned relative to each other in a generally uniform pattern. For example, FIGS. 7A-C shows four arms 146 spaced circumferentially apart from each other by about 90 degrees. The four arms 146 can be located generally symmetric about the cavity 152 (i.e., two arms 146a, 146b are located on one side, and two arms 146c, 146d are located on opposite side of the cavity 152).

In some embodiments, at least one arm 146 is circumferentially disposed between a pair of adjacent retaining members 142. For example, in the depicted embodiments, two arms 146a, 146d near the upper edge of the cavity 152 are located between two retaining members 142a, 142c, one arm 146b is located between the retaining members 142a and 142b, and one arm 146c is located between the retaining members 142b and 142c.

As shown in FIG. 7C, the valve alignment portion 120 can comprise a body 130 and a flange 116 connected to the proximal end of the body 130. The body 130 can have a generally cylindrical shape, except for having a cavity 132 extending from an outer periphery 134 of the body 130 through the central axis 112. Referring to FIG. 7B, the cavity 132 can have a width that is narrower near the central axis 112 (e.g., inner width W1) and wider near the periphery (e.g., outer width W1').

Figure 8:
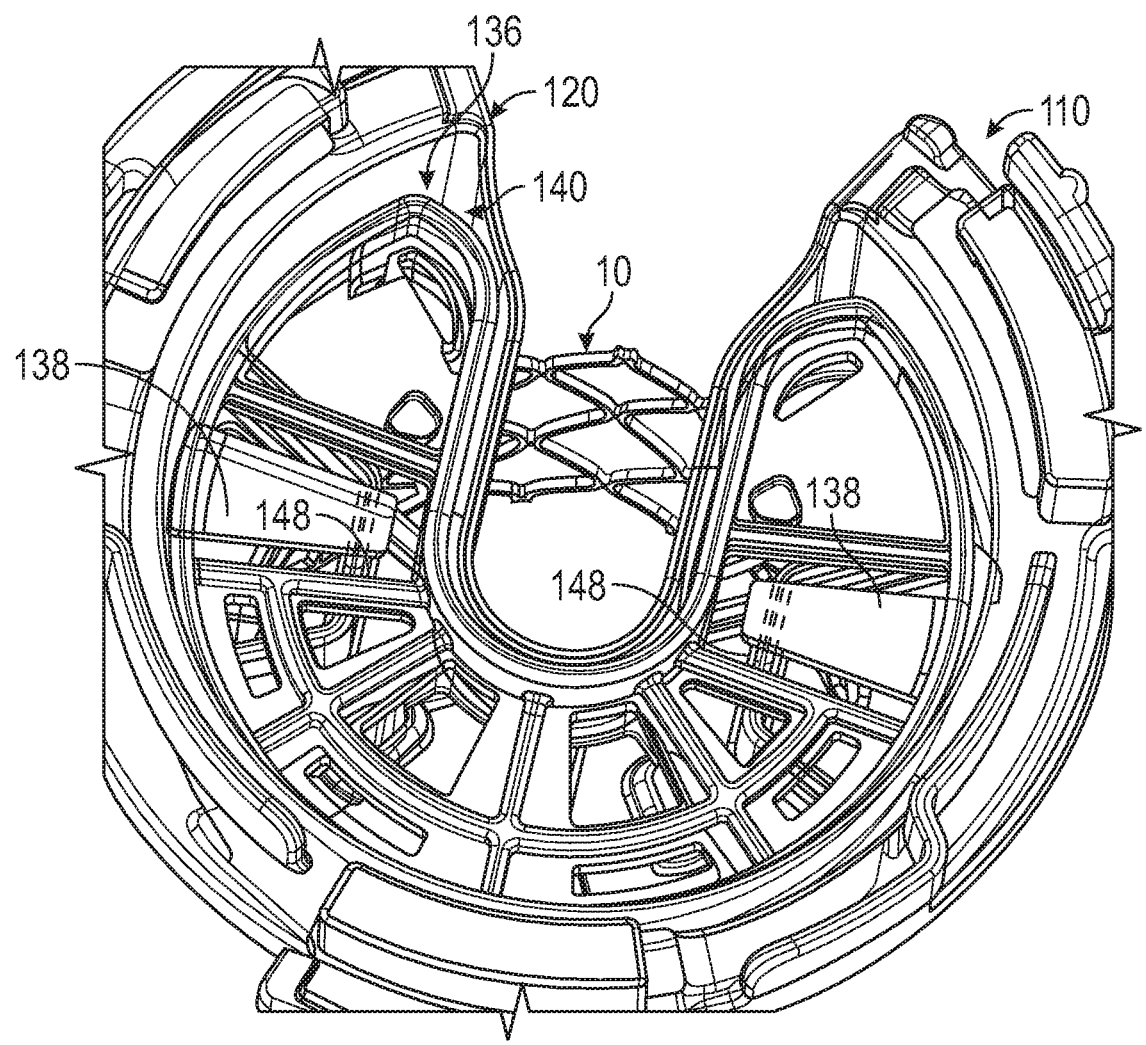
FIG. 8 shows a proximal perspective view of a holder device and a coupled prosthetic heart valve in the expanded configuration.

Generally, referring to FIG. 7B, the diameter D1 of the body 130 of the valve alignment portion 120 can be larger than the diameter D2 of the proximal plate 150 of the valve retaining portion 140. On the other hand, the width of the cavity 132 of the valve alignment portion 120 can be smaller than the width of the cavity 152 on the valve retaining portion 140 (e.g., W1<W2 and W1'<W2') so that the valve retaining portion 140 can be inserted into the valve alignment portion 120 as shown in FIG. 8.

Referring again to FIGS. 7C and 8, the body 130 of the valve alignment portion 120 can define a hollow interior space 136 opening to the proximal face of the body. The interior space 136 can be sized and shaped to accommodate the valve retaining portion 140, including the retaining members 142, the arms 146, and the proximal plate 150. As illustrated in FIG. 8, with a proper alignment between the cavity 152 of the valve retaining portion 140 and the cavity 132 of the valve alignment portion 120, the valve retaining portion 140 can be configured to slide into and/or out of the hollow interior space 136 through a proximal opening in the front face of the body 130.

The body 130 can further have a distal face 122 defining a wall of the hollow interior space 136. As shown, the distal face 122 can include a plurality of apertures 124 (e.g., four apertures 124a, 124b, 124c, and 124d are shown) that are respectively sized, shaped and positioned to receive the distal end portions of the plurality of arms 146 of the valve retaining portion 140. In addition, the body 130 can further include a plurality of auxiliary apertures 126 (e.g., three auxiliary apertures 126a, 126b, and 126c are shown) that are respectively sized, shaped and positioned to receive the distal end portions of the plurality of retaining members 142 of the valve retaining portion 140.

The auxiliary apertures 126 can be adjacent to and proximally recessed relative to the distal face 122. The auxiliary apertures 126 can be radially longer than the plurality of apertures 124. Each of the auxiliary apertures 126 can extend from the outer periphery 134 into the cavity 132 of the body 130.

The circumferential position of the apertures 124 and the auxiliary apertures 126 are configured to generally match the circumferential position of the corresponding arms 146 and the retaining members 142, respectively.

For example, the plurality of apertures 124 can be circumferentially positioned relative to each other in a generally uniform pattern. As shown in FIG. 7B, four apertures 124 can be circumferentially spaced apart from each other by about 90 degrees, and the four apertures 124 can be located generally symmetrically about the cavity 132 (i.e., two apertures 124a, 124b are located on one side and two apertures 124c, 124d are located on opposite side of the cavity 132).

Similarly, the plurality of auxiliary apertures 126 can be circumferentially positioned relative to each other in a generally uniform pattern. As shown, three auxiliary apertures 126 can be circumferentially spaced apart from each by about 120 degrees. Two of the auxiliary apertures 126a, 126c can be symmetrically located on opposite sides of the cavity 132, and the third auxiliary aperture 126b can be located diametrically opposite the cavity 132.

In certain embodiments, the distal face 122 can further include a plurality of recesses 128, each of which can extend from the outer periphery 134 into the cavity 132 of the body 130. As depicted in FIG. 7B, for example, two recesses 128 can be symmetrically located on opposite sides of the third auxiliary aperture 126b, each forming an angle of about 60 degrees with the third auxiliary aperture 126b.

With a proper alignment, the valve retaining portion 140 can be inserted into the valve alignment portion 120 such that the plurality of arms 146 can extend through the corresponding apertures 124 and the plurality of retaining members 142 can extend through the corresponding auxiliary apertures 126, as shown in FIG. 7A. Thus, distal movement of the valve retaining portion 140 relative to the valve alignment portion 120 can push the distal end portions of the arms 146 and the distal end portions of the retaining members 142 distally relative to the distal face 122 of the valve alignment portion 120. Conversely, proximal movement of the valve retaining portion 140 relative to the valve alignment portion 120 can withdraw the distal end portions of the arms 146 and the distal end portions of the retaining members 142 proximally relative to the distal face 122 of the valve alignment portion 120.

Although the embodiments depicted in FIGS. 7A-C show four arms 146 (and four corresponding apertures) as well as three retaining members 142 (and three corresponding auxiliary apertures 126), it should be understood that any number of arms (and the corresponding apertures) and any number of retaining members (and the corresponding auxiliary apertures) can be used. Further, the arms (and the corresponding apertures) and the retaining members (and the corresponding auxiliary apertures) need not be equally circumferentially spaced from each other.

Valve-Holder Interface

As noted above, a radially expandable and compressible prosthetic implant can be releasably coupled to the holder device 110. Specifically, a prosthetic implant, such as the prosthetic heart valve 10, can be releasably coupled to the valve retaining portion 140 and positioned distally relative to the valve alignment portion 120 of the holder device 110.

Figure 9A:
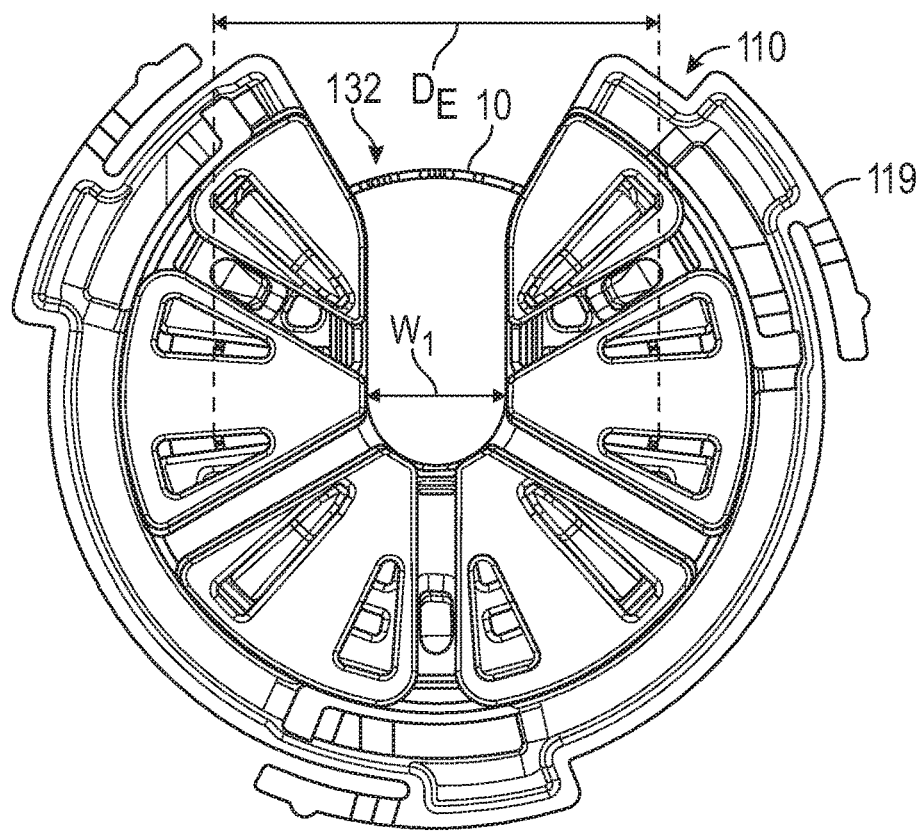
FIG. 9A shows a distal end view of a holder device and a coupled prosthetic heart valve in the expanded configuration.
Figure 9B:
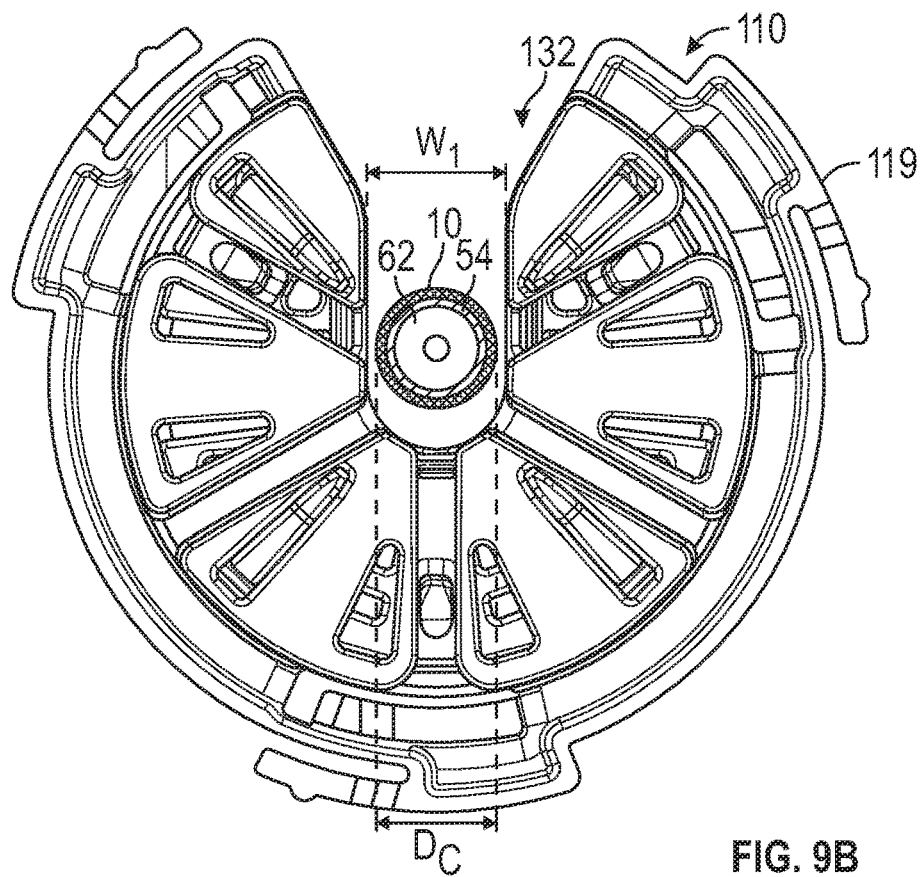
FIG. 9B shows a distal end view of a holder device and a prosthetic heart valve in a compressed configuration.

For example, FIGS. 8 and 9A show different views of the holder device 110 holding the prosthetic heart valve 10 in an expanded configuration. FIG. 9B shows the holder device 110 after the prosthetic heart valve 10 is removed from the holder device 110 and crimped onto the balloon 54 of the delivery apparatus 50.

When the prosthetic heart valve 10 is in the expanded configuration, the diameter DE of the prosthetic heart valve 10 can be generally larger than the inner width W1 of the cavity 132 (see, e.g., FIG. 9A). Thus, the holder device 110 can prevent the proximal movement of the prosthetic heart valve 10 when it is in the expanded configuration. However, when the prosthetic heart valve 10 is in the compressed configuration, the diameter Dc of the prosthetic heart valve 10 can be smaller than the inner width W1 of the cavity 132 (see, e.g., FIG. 9B). Thus, after crimping, the delivery apparatus 50, together with the prosthetic heart valve 10 crimped thereon, can be withdrawn proximally out of the holder device 110 through the cavity 132.

In some embodiments, the holder device 110 can comprise a biasing mechanism that biases the valve retaining portion 140 proximally relative to the valve alignment portion 120. In one example, FIG. 8 shows two biasing members 138 located on the valve retaining portion 140 interfacing with respective adjacent surfaces located on the valve alignment portion 120, which can be in the form of piston members 148.

When the retaining members 142 are coupled to the prosthetic heart valve 10, the biasing members 138, such as spring plates or bias springs, can be preloaded and exert a biasing force against the contacting piston members 148. When the retaining members 142 are pushed inwardly by the crimping jaws 170 relative to the prosthetic heart valve 10, the biasing force from the biasing members 138 moves the valve retaining portion proximally relative to the valve alignment portion so as to move the retaining arms proximally out of the prosthetic valve. The biasing mechanism can be implemented by means of any mechanical and/or non-mechanical means, such as the electro-magnetic repelling force generated between two magnets with like poles (not shown). In addition, any number of biasing members can be employed in the holder device. The biasing members can also be separate components from the valve alignment portion 120 and the valve retaining portion 140.

Figure 10:
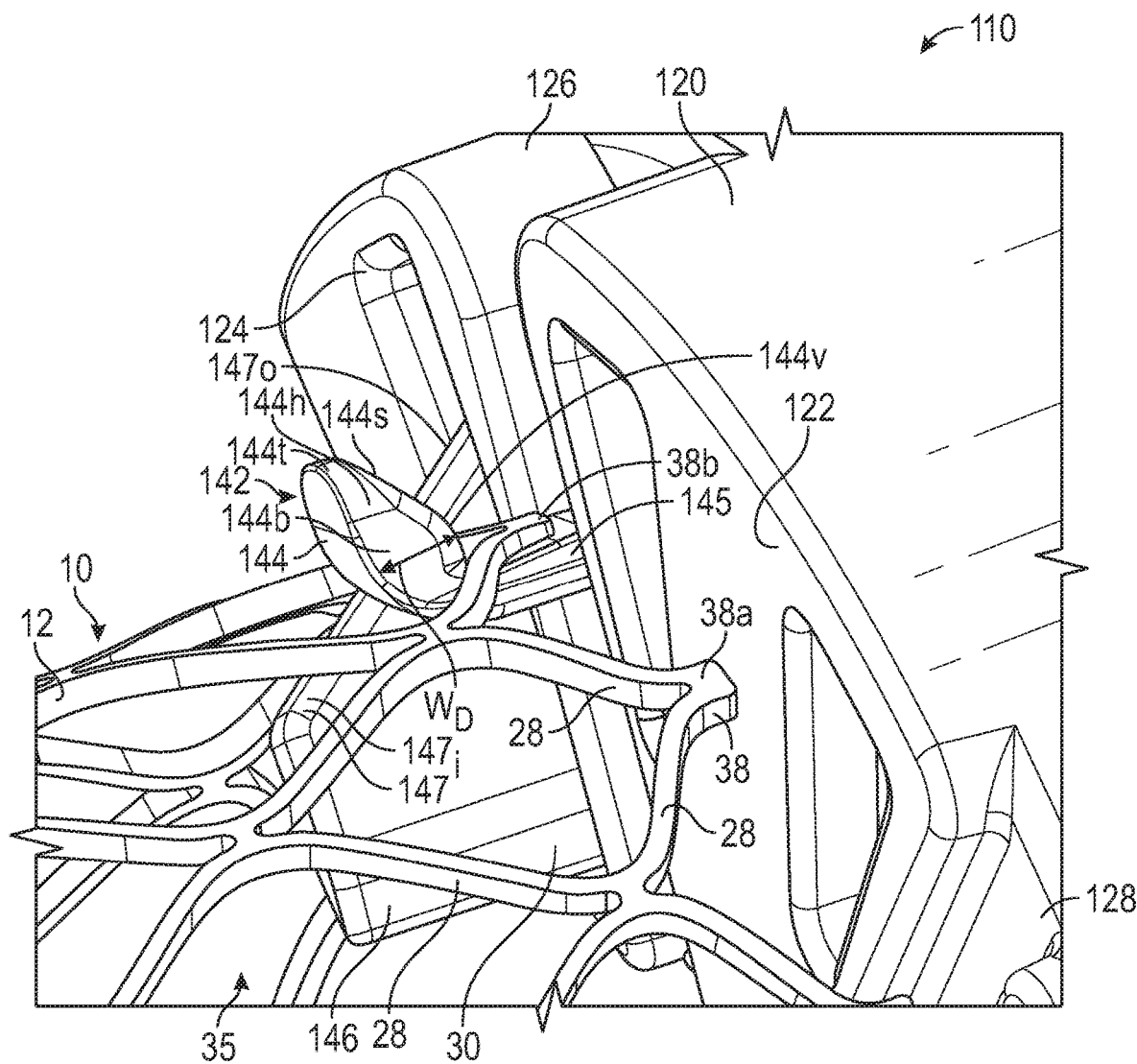
FIG. 10 shows an enlarged view of a portion of the coupling interface between a prosthetic heart valve and a holder device, according to one embodiment.

FIG. 10 shows an enlarged view of a portion of the coupling interface between the prosthetic heart valve 10 and the holder device 110, according to one embodiment. The prosthetic heart valve 10 is shown in the expanded configuration defining an interior space 35.

As described above, each retaining member 142 can comprise a protrusion 144 which extends radially outwardly from the distal end portion of the beam 145. Each of the cantilevered beams 145 can be preloaded or biased to the outward direction. Thus, each of the protrusions 144 can extend from the interior space 35 of the prosthetic heart valve 10, through a portion of the prosthetic heart valve, to a location outside of the prosthetic heart valve 10 when the prosthetic heart valve 10 is in the expanded configuration. In this manner, the retaining members 142 can hook the prosthetic heart valve 10 onto the holder device 110.

In some embodiments, each protrusion 144 can comprise a base portion 144b which joins the distal end portion of the beam 145 and a head portion 144h that projects radially outwardly relative to the base portion 144b. In some embodiments, the base portion 144b can have a proximal surface 144v that extends radially outwardly and generally perpendicular to the beam 145. In some embodiments, the head portion 144h can have a proximal sloped surface 144s which tilts or curves toward a tip portion 144t. The proximal sloped surface 144s can extend from the proximal vertical surface 144v to the tip portion 144t.

In some embodiments, the base portion 144b can have a larger longitudinal dimension WD than the tip portion 144t. In some embodiments, the protrusion 144 can have a generally tapered shape such that its longitudinal dimension WD progressively decreases from the base portion 144b to the tip portion 144t.

As shown in FIG. 10, the proximal end portion of the prosthetic heart valve 10 can be defined by a plurality of proximal nodes or apices 38 of the frame 12, each of which can be formed at the intersection of two circumferentially adjacent angled struts 28 of the frame. As shown, each protrusion 144 can extend radially outwardly through an adjacent open cell 30. In addition, the beams 145 can be preloaded such that they are biased radially outward against the inner surface of the frame 12. Thus, the retaining members 142 in the illustrated embodiment can securely hold the frame 12 (and thus the prosthetic valve) on the holding device via the outward biasing force of the retaining members as well as by the protrusions 144 hooking onto the struts of the frame at selected apices 38.

As described above, one or more biasing members can be incorporated into the holder device 110 so as to bias the valve retaining portion 140 proximally relative to the valve alignment portion 120. Also, the proximal surface 144v of the base portion 144b can engage an adjacent proximal node 38 and two angled struts 28 intersecting at that node 38. As such, the biasing members urge the retaining members 142 proximally, which in turn urge the frame 12 against the distal face 122 of the valve alignment portion 120.

As shown in FIG. 10, at least some of the proximal nodes 38 (e.g., 38a) are in direct contact with the distal face 122 of the valve alignment portion 120 of the holder device 110. Thus, despite the force (in the proximal direction) applied to the frame 12 by the protrusion 144, the distal face 122 can block proximal movement of the frame 12 so long as the prosthetic heart valve 10 is not in the compressed configuration (note: in the compressed configuration, all proximal nodes 38 are located within the cavity 132 because the diameter of the prosthetic heart valve 10 is smaller than the inner width of the cavity 132, as noted above.). Nonetheless, the force applied by the retaining members 142 can keep those proximal nodes 38a in contact with the distal face 122.

In some embodiments, some of the proximal nodes 38 (e.g., 38b) may be aligned with the cavity 132, the auxiliary apertures 126, or the recesses 128, such that they do not directly contact the distal face 122. Nonetheless, all proximal nodes 38a, 38b can be generally coplanar with the distal face 122.

As shown in FIG. 10, each arm 146 of the holder device 110 can comprise a sloped surface 147 along the distal end portion of the arm 146. The sloped surface 147 can be oriented to face partially outwardly in the radial direction and partially distally in the axial direction. When the prosthetic heart valve 10 is in the expanded configuration, at least an inner portion 147i of the sloped surface 147 can extend into the interior space 35 of the prosthetic heart valve 10. In addition, an outer portion 147o of the sloped surface 147 can be located radially outward relative to the frame 12, as well distal relative to the distal face 122 of the valve alignment portion 120.

In some embodiments, the retaining members 142 can extend radially outwardly relative to the arms 146 when the prosthetic heart valve 10 is in the expanded configuration. For example, the tip portion 144t of the protrusion 144 can extend radially outwardly relative to the sloped surface 147 (including the outer portion 147o) of the arm 146 when the prosthetic heart valve 10 is in the expanded configuration.

When the prosthetic heart valve 10 is crimped from the expanded configuration to the compressed configuration with the crimping device 160, the jaws 170 of the crimping device 160 press the retaining members 142 of the holder device 110 radially inwardly into the interior space 35 of the prosthetic heart valve 10. The jaws 170 also move the arms 146 and thus the valve retaining portion 140 axially proximally relative to the prosthetic heart valve 10 until the retaining members 142 are withdrawn from the prosthetic valve. Continued movement of the jaws 170 crimps the prosthetic valve onto the delivery apparatus. In this manner, the prosthetic heart valve is released from the valve holder 110 as the crimping device 160 is actuated. This process is further described below.

Figure 11A:
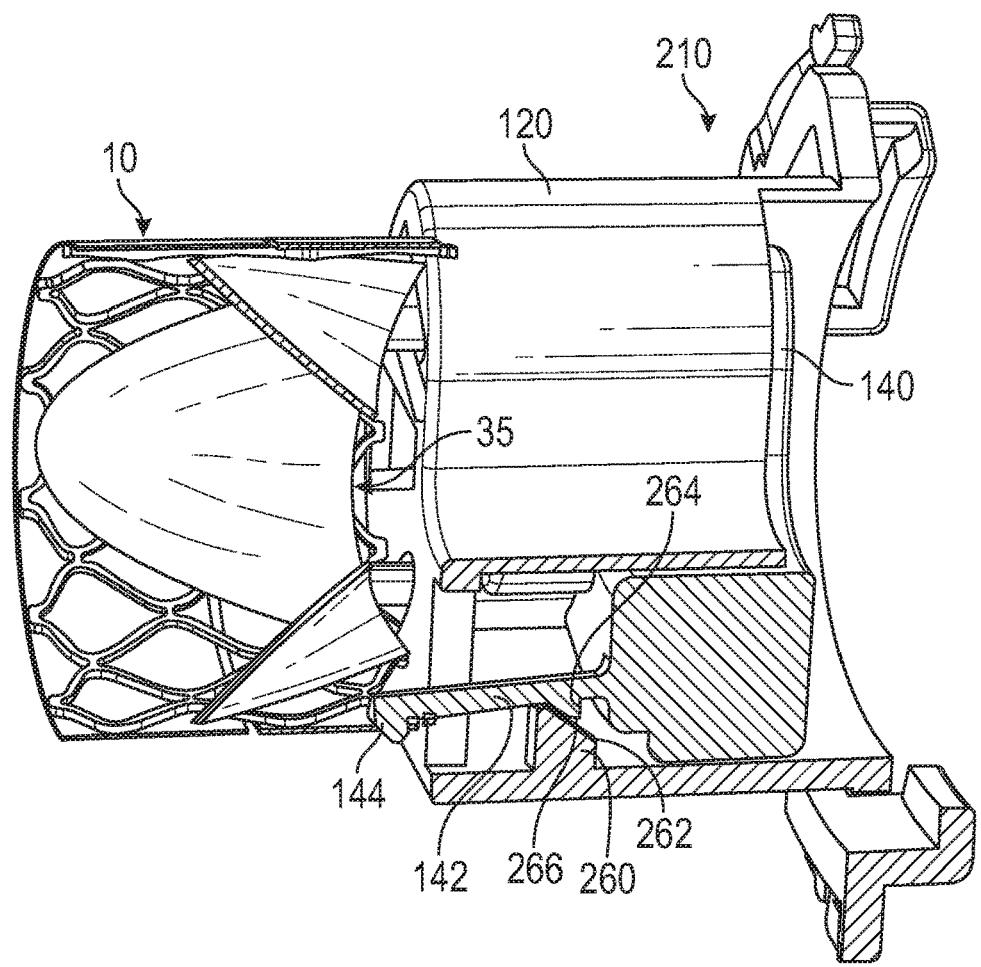
FIG. 11A shows the prosthetic heart valve coupled to a holder device, according to another embodiment.

FIG. 11A shows the prosthetic heart valve 10 coupled to another embodiment of a holder device 210, which has a similar structure and valve-interface as the holder device 110. For example, the holder device 210 can also comprise the valve alignment portion 120 and the valve retaining portion 140 as shown in FIGS. 7A-7C, except for some additional features as described below.

As shown in FIG. 11A, the holder device 210 can include a ramped interface for each of the retaining members 142. Specifically, the valve alignment portion 120 of the holder device 210 can include a plurality of inwardly extending sloped projections 260. Each sloped projection 260 can be positioned radially outward relative to a corresponding retaining member 142. Each sloped projection 260 can have a sloped inner surface 262 which is oriented to face partially radially inwardly and partially axially proximally.

Correspondingly, each retaining member 142 can have a sloped protrusion 264 adjacent a corresponding projection 260. Each sloped protrusion 264 can have a sloped outer surface 266 which is oriented to face partially radially outwardly and partially axially distally. The sloped outer surface 266 can be complementarily positioned, sized, and shaped relative to the corresponding sloped inner surface 262 of an adjacent projection 260. Thus, the sloped projection 260 can be configured to interface with the corresponding sloped protrusion 264 by a sliding engagement between the sloped inner surface 262 and the sloped outer surface 266.

Figure 11B:
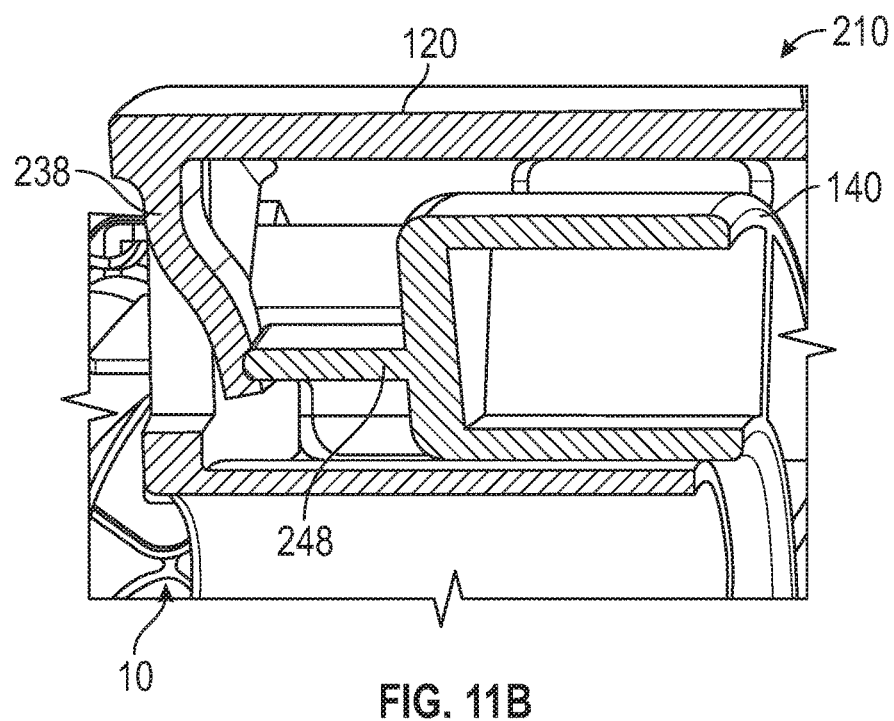
FIG. 11B shows a biasing mechanism in the holder device of FIG. 11A.

The holder device 210 can also include a biasing mechanism that biases the valve retaining portion 140 proximally relative to the valve alignment portion 120. FIG. 11B shows an alternative embodiment of the biasing mechanism, where a biasing member 238 located on the valve alignment portion 120 of the holder device 210 interfaces with a corresponding piston member 248 located on the valve retaining portion 140 of the holder device 210. When the retaining members 142 are coupled to the prosthetic heart valve 10, the biasing member 238 is pushed distally to a loaded position by the piston member 248. When the retaining members 142 are released from the prosthetic heart valve 10, the biasing member 238 returns to its unloaded position and pushes the piston member 148 in the proximal direction.

To mount the prosthetic heart valve 10 to the holder device 210, the valve retaining portion 140 can be moved distally relative to the valve alignment portion 120. Due to the ramped interfaces between the retaining members 142 and the corresponding sloped projections 260, the distal end portions of the retaining members 142 (including the protrusions 144) move radially inwardly so that they can be easily inserted into the interior space 35 of the prosthetic heart valve 10 when the prosthetic heart valve 10 is in the expanded configuration. Then, as the cantilevered beams 145 tilt outwardly and return toward their preloaded positions, the protrusions 144 can "grab" the prosthetic heart valve 10 by extending from the interior space 35 of the prosthetic heart valve 10, through an opening of the frame 12, to a location outside of the prosthetic heart valve 10.

Conversely, when the retaining members 142 are released from the prosthetic heart valve 10, e.g., during the crimping process as describe more fully below, the valve retaining portion 140 can be urged to move in the proximal direction relative to the valve alignment portion 120, such as under the force of the biasing member 238 and/or through contact between the crimping jaws 170 and ramped arms 146 (the ramped arms 146 are optional in the embodiment of FIGS. 11A-11B). As the valve retaining portion 140 is moved proximally, the distal end portions of the retaining members 142 move radially inwardly relative to the prosthetic valve to release from the cells 30 of the frame due to the ramped surfaces. Continued movement of the valve retaining portion 140 withdraws the distal end portions of the retaining members 142 out of the interior space 35 of the prosthetic heart valve 10.

Crimping Process

Figure 12A:
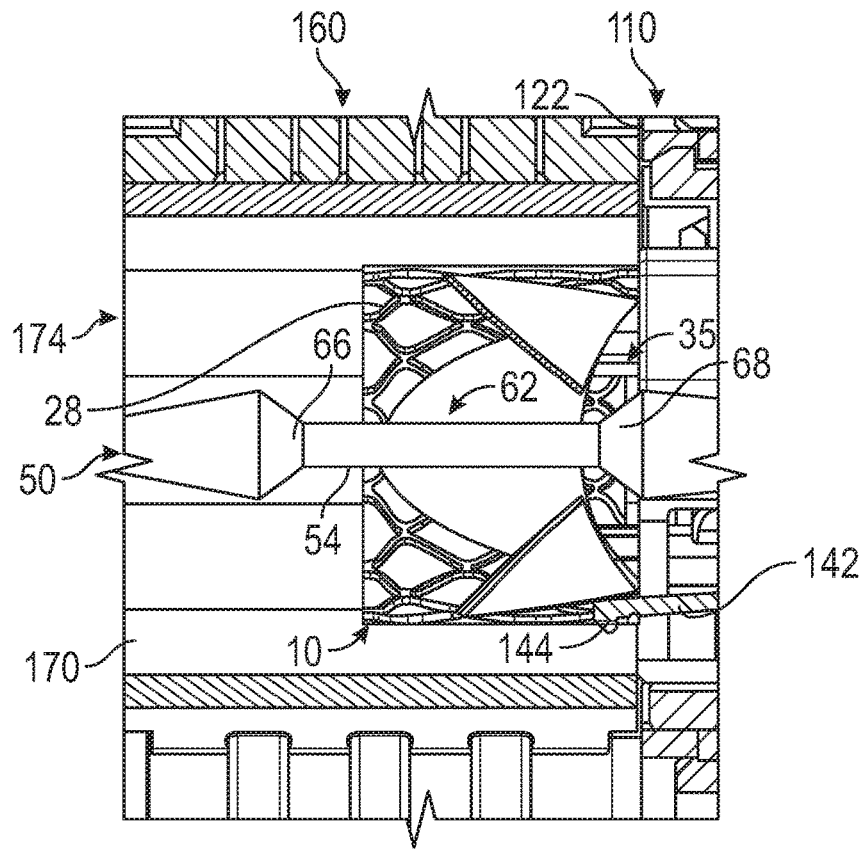
FIGS. 12A and 12B is a cross-sectional view of a crimping device with a prosthetic valve and the distal end portion of a delivery apparatus inside of the crimping device.
Figure 12B:
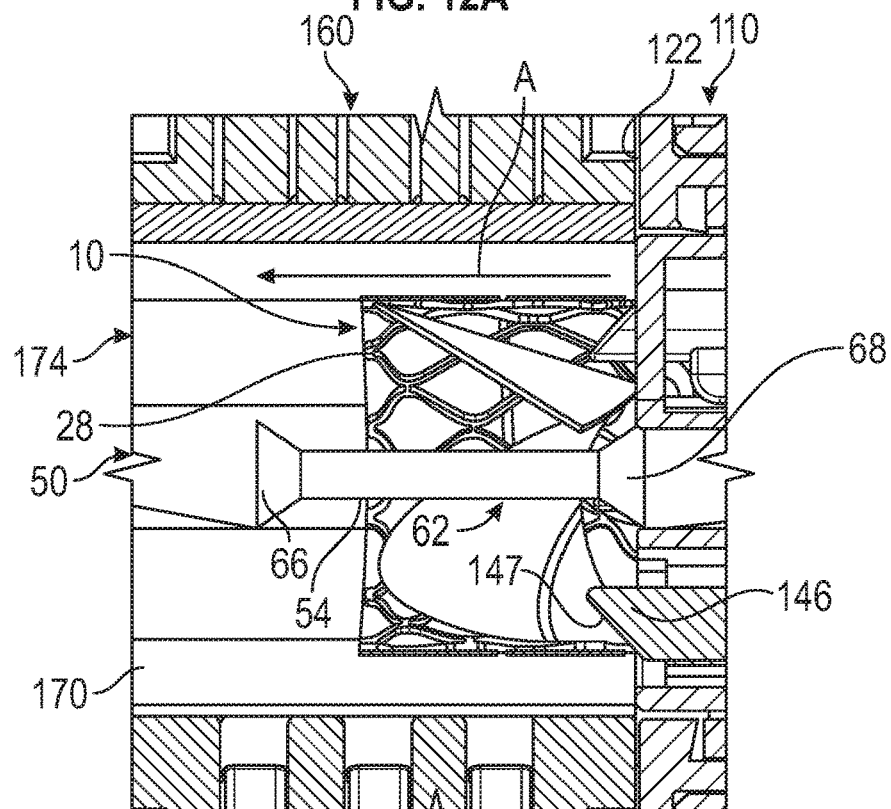

FIGS. 12A-B illustrate a method of crimping the prosthetic heart valve 10 onto the delivery apparatus 50. In the depicted embodiment, when the holder device 110 is coupled to the crimping device 160, the proximal edge of the jaws 170 of the crimping device 160 are aligned with the distal face 122 of the valve alignment portion 120.

As illustrated in FIG. 12A, during actuation of the crimping device 160, the closing jaws 170 of the crimping device 160 can first contact the tip portion 144$t$ of each protrusion 144 (which are outside of the prosthetic heart valve). As the jaws 170 further close to reduce the size of the crimping aperture 174, the jaws push the protrusions 144 radially inwardly relative to the frame 12. After the proximal surface 144$v$ of the base portion 144$b$ is pushed into the interior space 35 of the prosthetic heart valve 10, the gripping force applied to the frame 12 by the protrusions 144 decreases because the frame 12 now interfaces with the proximal sloped surface 144$s$ of the head portion 144$h$. Because the biasing members in the holder device 110 can urge the retaining members 142 in the proximal direction, the protrusions 144 can slide off and release their grip of the frame 12 as they move proximally under the force of the biasing members.

As the jaws 170 continue to close radially inwardly, the jaws 170 can interface with and slide on the sloped surfaces 147 of the arms 146. For example, the closing jaws 170 can contact the outer portions 147$o$ of the sloped surfaces 147 and slide radially inwardly on the sloped surfaces 147. As a result, the closing jaws 170 can exert a force to the sloped surfaces 147 and move the arms 146 and thus the retaining members 142 in the proximal direction relative to the valve alignment portion 120. As the distal end portions of the arms 146 withdraw proximally from the interior space 35 of the prosthetic heart valve 10, the closing jaws 170 can contact the frame 12 and apply radially inward pressure to the frame 12. As a result, the prosthetic heart valve 10 can be radially compressed. When the arms 146 (and the retaining members 142) are completed ejected out of the interior space 34, the prosthetic heart valve 10 can be fully crimped to the compressed configuration on the delivery apparatus.

Crimping the prosthetic heart valve 10 can cause axial elongation of the frame 12. However, the frame 12 can only elongate in the distal direction (i.e., the direction indicated by arrow A in FIG. 12B) because the proximal end portion of the prosthetic heart valve 10 can remain contact with the distal face 122 of the valve alignment portion 120 as the prosthetic heart valve 10 is radially compressed from the expanded configuration with the crimping device 160. As noted above, at least some of the proximal nodes 38$a$ of the frame 12 abut the distal face 122 of the valve alignment portion 120 so long as the prosthetic heart valve 10 is not in the compressed configuration. Thus, the distal face 122 can serve as barrier that prevents the frame 12 from elongating in the proximal direction during the crimping process.

As shown in FIGS. 12A-12B, the holder device 110 can be so configured that the distal face 122 of the valve alignment portion 120 is aligned with the proximal end 68 of the valve mounting portion 62 when the holder device 110 is coupled to the positioning device 180 mounted on the delivery apparatus 50. Thus, the proximal end of the prosthetic heart valve 10 can be precisely aligned with the proximal end 68 of the valve mounting portion 62 during the crimping process. As noted above, the axial length L of the valve mounting portion 62 can be approximately equal to the axial length of the prosthetic heart valve 10 when it is in the compressed configuration. Because the prosthetic valve is prevented from elongating in the proximal direction, when the prosthetic heart valve 10 is fully compressed, the distal end of the prosthetic heart valve 10 can become precisely aligned with the distal end 66 of the valve mounting portion 62. Therefore, the disclosed assembly of devices and methods can, for example, support fast, easy, and accurate crimping of the prosthetic heart valve 10 on the balloon 54 of the delivery apparatus 50.

Alternative Embodiments

Figure 15A:
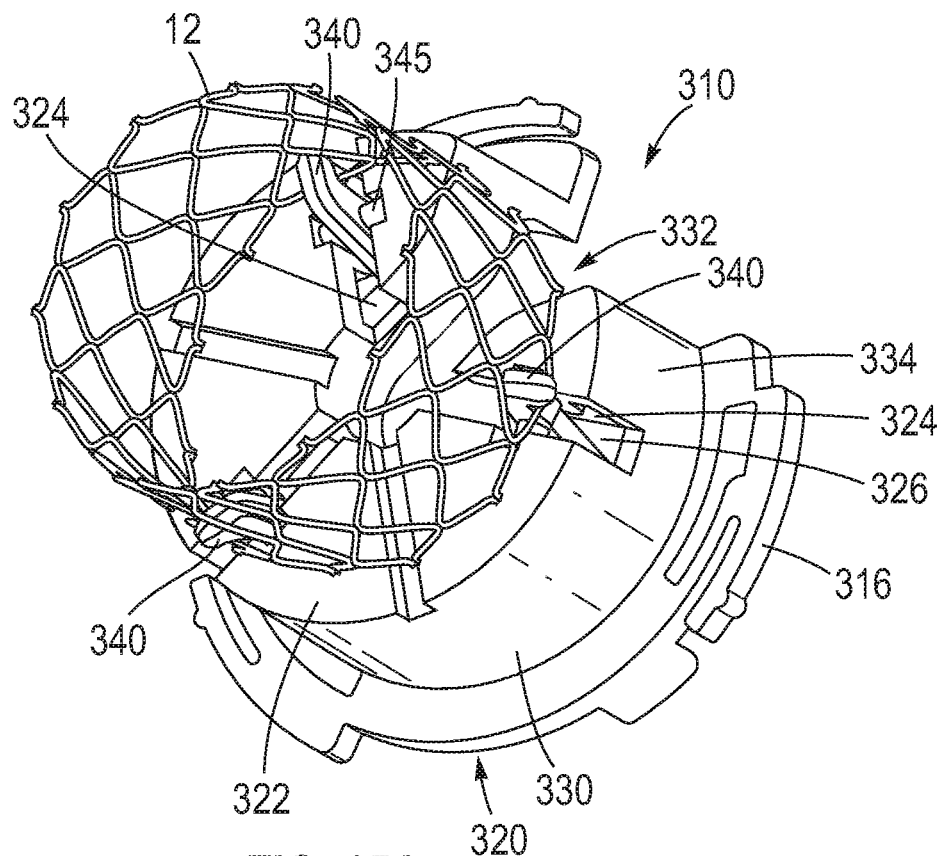
FIG. 15A is a perspective view of another embodiment of a holder device and a frame of a prosthetic heart valve coupled to the holder device via a plurality of valve retaining members.
Figure 15B:
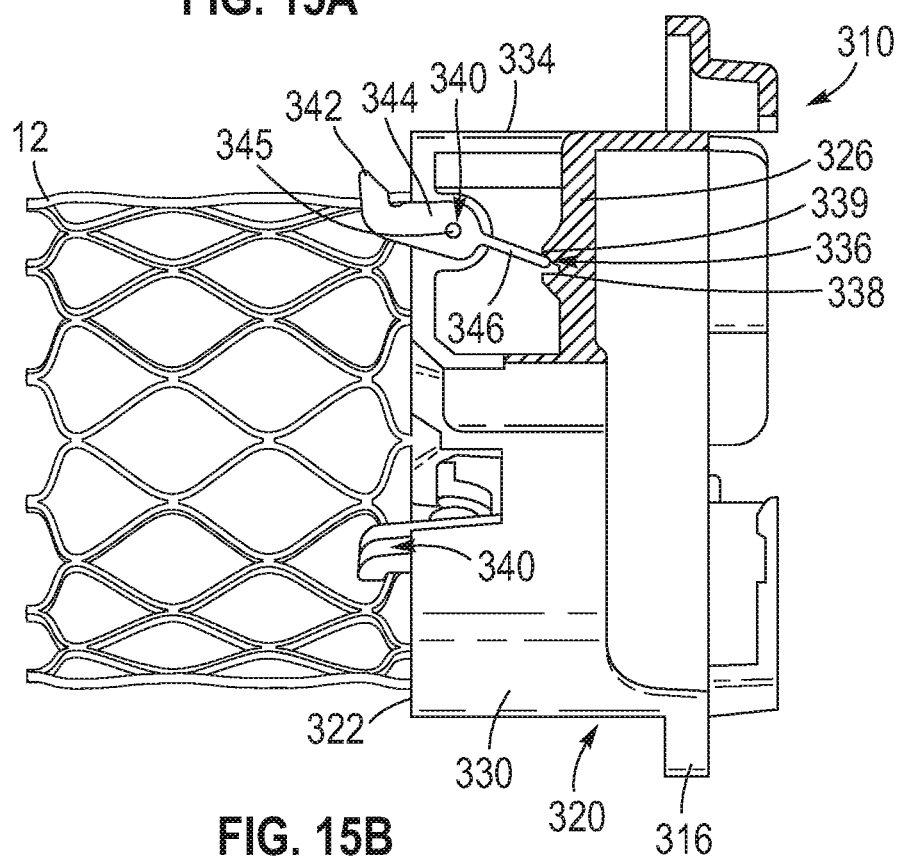
FIG. 15B is a cross-sectional view of the frame and the holder device depicted in FIG. 15A, wherein the plurality of valve retaining members are shown in valve-engaging position.

FIGS. 15A-15B show the frame 12 of a prosthetic heart valve coupled to another embodiment of a holder device 310, which has a different valve retaining and releasing mechanism. The holder device 310 includes a valve alignment portion 320 and one or more valve retaining members 340. In the depicted embodiments, three valve retaining members 340 are shown, although it should be understood that one, two, or more than three valve retaining members 340 can be included. Each valve retaining member 340 can include a head portion 342, a body portion 344, and a tail portion 346.

The valve alignment portion 320 can have a body portion 330 and a flange 316 connected to the proximal end of the body portion 330. The flange 316 can be configured to releasably couple to a positioning device 180 and/or a crimping device 160, as described above. The body portion 330 can have a generally cylindrical shape, except for having a cavity 332 extending from an outer periphery 334 of the body portion 330 through its central axis.

The body portion 330 has a distal face 322 which can include a plurality of apertures 324. For example, in the embodiment depicted in FIG. 15A, three apertures 324 are spaced circumferentially apart from each other by about 120 degrees. Two of the apertures 324 can be symmetrically located on opposite sides of the cavity 332, and the third aperture 324 can be located diametrically opposite the cavity 332.

The body portion 330 can have a plurality of inner panels 326 that are located between the distal face 322 and the flange 316, and extend radially inwardly from the outer periphery 334. As shown in in FIG. 15A, each inner panel 326 can be positioned and oriented so that it is proximal and opposite to a corresponding aperture 324.

Figure 15D:
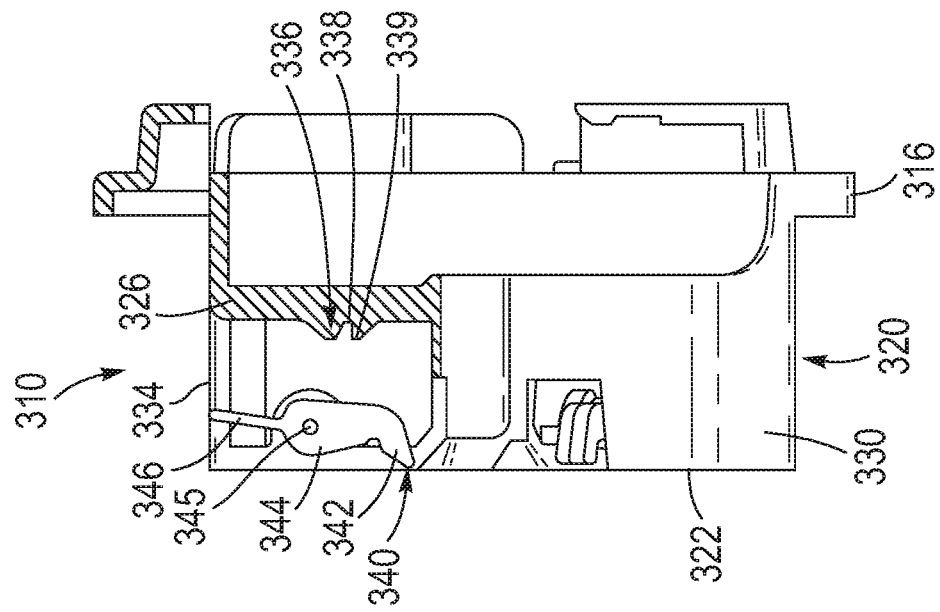
FIG. 15D is a cross-sectional view of the holder device depicted in FIG. 15A without showing the frame, wherein the plurality of valve retaining members are shown in stowed position.
Figure 15C:
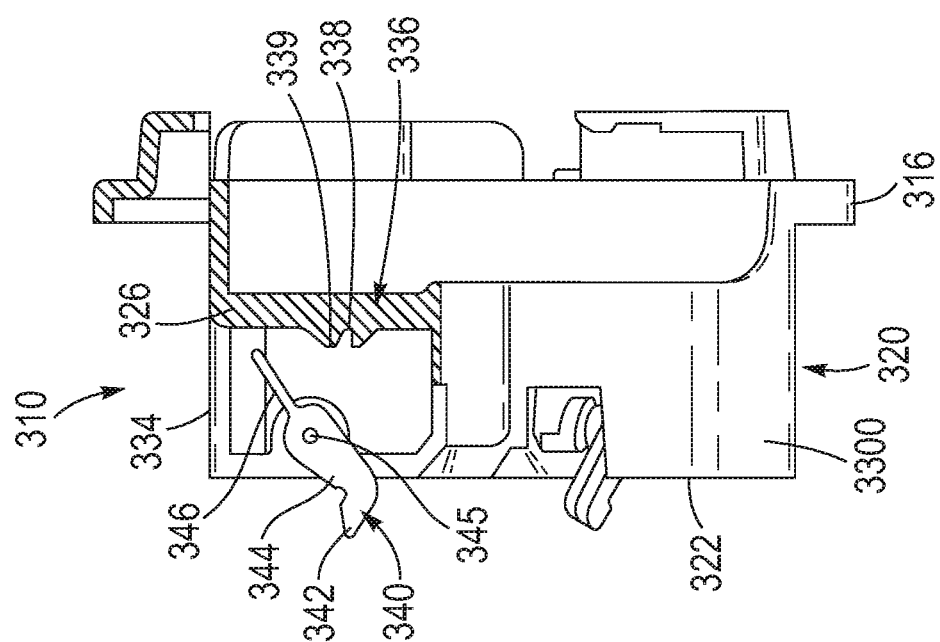
FIG. 15C is a cross-sectional view of the holder device depicted in FIG. 15A without showing the frame, wherein the plurality of valve retaining members are shown in valve-releasing position.

As described below, the valve retaining members 340 can be transitioned from a valve-engaging position as shown in FIGS. 15A-15B, through a valve-releasing position as shown in FIG. 15C, to a stowed position as shown in FIG. 15D.

In the valve-engaging position (see e.g., FIGS. 15A-15B), each valve retaining member 340 can extend axially from a corresponding inner panel 326 and through a corresponding aperture 324 on the distal face 322. The head portion 342 projects radially outwardly relative to the body portion 344 and the tail portion 346, and the tail portions 346 are coupled to the corresponding inner panels 326. Specifically, each head portion 342 can extend radially outwardly through an open frame cell of the prosthetic heart valve. As such, the head portion 342 can grip a strut segment of the frame 12 and retain the prosthetic heart valve in the radially expanded configuration.

In the depicted embodiment, each inner panel 326 includes a ledge member 336, and the tail portion 346 of the valve retaining member 340 is configured to be releasably secured to the ledge member 336. For example, the proximal end portion of the tail portion 346 can be received in a groove 338 located in the middle of the ledge member 336, and the ridges 339 surrounding the groove 338 can prevent the tail portion 346 from escaping from the groove 338 when there is no or insufficient force being applied to the tail portion 346.

In some embodiments, the body portion 344 of the valve retaining member 340 is hingedly connected to the body portion 330 of the valve alignment portion 320. For example, in the embodiment depicted in FIGS. 15A-15B, the body portion 344 of the valve retaining member 340 includes a hinge 345 which extends across the adjacent aperture 324 and is coupled to the distal face 322. As such, when the tail portion 346 of the valve alignment portion 320 is detached from the ledge member 336 (e.g., escape from the groove 338), the valve alignment portion 320 can pivot about the hinge 345.

Crimping of the prosthetic valve can be achieved by actuation of the crimping device 160 as described above. The closing jaws 170 of the crimping device 160 can press the head portion 342 of the valve retaining member 340 radially inwardly relative to the frame 12. After the head portion 342 loses grip of the frame 12, the valve retaining member 340 is transitioned to the valve-releasing position (see e.g., FIG. 15C), and the prosthetic valve can be crimped to the radially compressed configuration.

When the closing jaws 170 apply enough force to the head portion 342, the force can be transmitted to the tail portion 346, causing the tail portion 346 to overcome the resistance of ridges 339 and detach from the ledge member 336. In some embodiments, the tail portion 346 can comprise an elastic material so that the tail portion 346 can deflect slightly in response to the applied force, thus facilitating the tail portion 346 to detach from the ledge member 336.

As the jaws 170 continue to close during the crimping process, the jaws 170 can keep pushing the head portion 342 radially inwardly, causing the corresponding valve retaining member 340 to rotate around the hinge 345 until the head portion 342 is located proximal to the distal face 322, and the valve retaining member 340 is transitioned to the stowed position (see e.g., FIG. 15D).

In some embodiments, the valve retaining member 340 can include a bias member (not shown) which is so configured that the valve retaining member 340 is biased when it is in the valve-engaging position and unbiased when it is in the stowed position. As such, after the tail portion 346 is detached from the ledge member 336, the biasing force can cause or facilitate the valve retaining member 340 to move to the stowed position. When all the valve retaining members 340 are in the stowed position, the prosthetic heart valve can be fully crimped to the compressed configuration on the delivery apparatus.

FIGS. 16A-16D show an alternative embodiment of a holder device 410 for retaining and releasing the frame 12 of a prosthetic valve. The holder device 410 includes a valve alignment portion 420 and one or more valve retaining members 440. In the depicted embodiments, three valve retaining members 440 are shown, although it should be understood that one, two, or more than three valve retaining members 440 can be included.

As shown in FIG. 16B, the valve alignment portion 420 can have a body portion 430 and a flange 416 connected to the proximal end of the body portion 430. The flange 416 can be configured to releasably couple to a positioning device 180 and/or a crimping device 160, as described above. The body portion 430 can have a generally cylindrical shape, except for having a cavity 432 extending from an outer periphery 434 of the body portion 430 through its central axis. The body portion 430 has a distal face 422 which can include a plurality of apertures 424. For example, FIG. 16B shows seven apertures 424 on the distal face 422.

As shown in FIG. 16A, each valve retaining member 440 can include a base portion 442, a first leg 444, and a second leg 446. The first and second legs 444, 446 can extend from the base portion 442 and form two cantilevers. The distal end portion of each leg 444, 446 can be deflected upon applying a force perpendicular to the leg. The base portion 442 is positioned proximal to the flange 416, and the first and second legs 444, 446 can extend through the valve alignment portion 420, and further extend distally of the distal face 422 through two adjacent apertures 424.

The first leg 444 is generally perpendicular to the base portion 442. A distal end portion 447 of the first leg 444 can include a ledge 448. The distance between the ledge 448 and the base portion 442 is about the same or slightly longer than the axial length of the valve alignment portion 420 such that when the base portion 442 abuts or is adjacent to the proximal end of the flange 416, the distal end portion 447 of the first leg 444 is distal to the distal face 422 and the ledge 448 can lean against the distal face 422 at a location adjacent the aperture through which the first leg 444 extends. When the ledge 448 leans against the distal face 422, the valve retaining member 440 is releasably coupled to the valve alignment portion 420, and is restricted from axial movement relative to the valve alignment portion 420.

The second leg 446 includes a proximal portion 450 that is generally parallel to the first leg 444 and a distal portion 452 that is angled relative to and tilts away from the first leg 444. A tip portion 454 of the distal portion 452 can extend radially outwardly so as to form a notch or hook 456 that can engage a portion of the frame 12. When the first and second legs 444, 446 extend through two adjacent apertures 424, the tip portion of the second leg 446 is configured to extend radially outwardly through an open frame cell of the prosthetic heart valve. As such, the notch 456 on the second leg 446 can grip a strut segment of the frame 12 and retain the prosthetic heart valve in the radially expanded configuration (see e.g., FIG. 16B).

In some embodiments, the frame 12 can be held away from the holder device 410. For example, when the frame 12 is retained by the valve retaining members 440 in the radially expanded configuration (FIG. 16C) or during the crimping process (FIG. 16D), the proximal end of the frame 12 can be spaced apart from the distal face 422 by a predetermined distance.

Figure 16D:
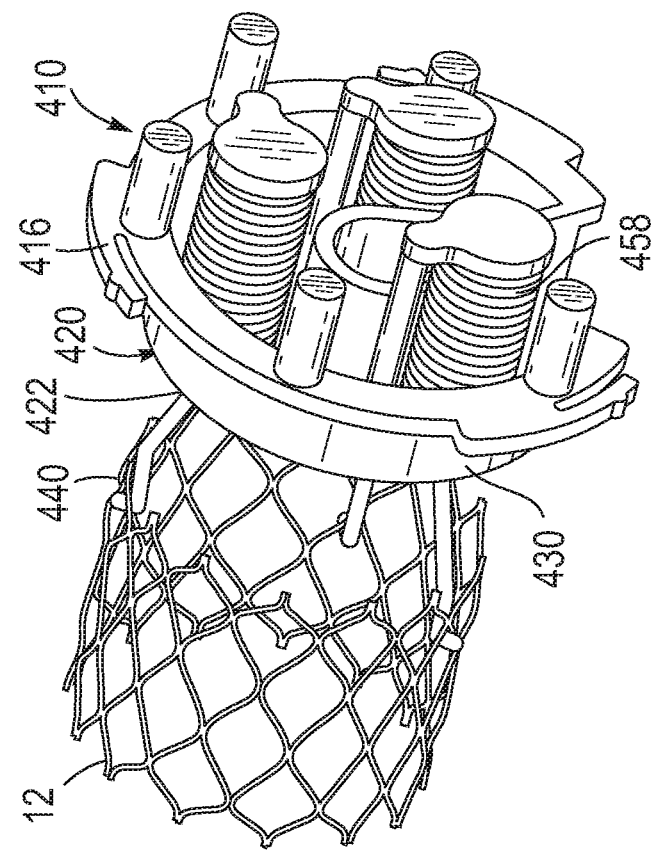
FIG. 16D is a rear perspective view of the holder device and the frame as depicted in FIG. 16B, wherein the frame is decoupled from the holder device.
Figure 16C:
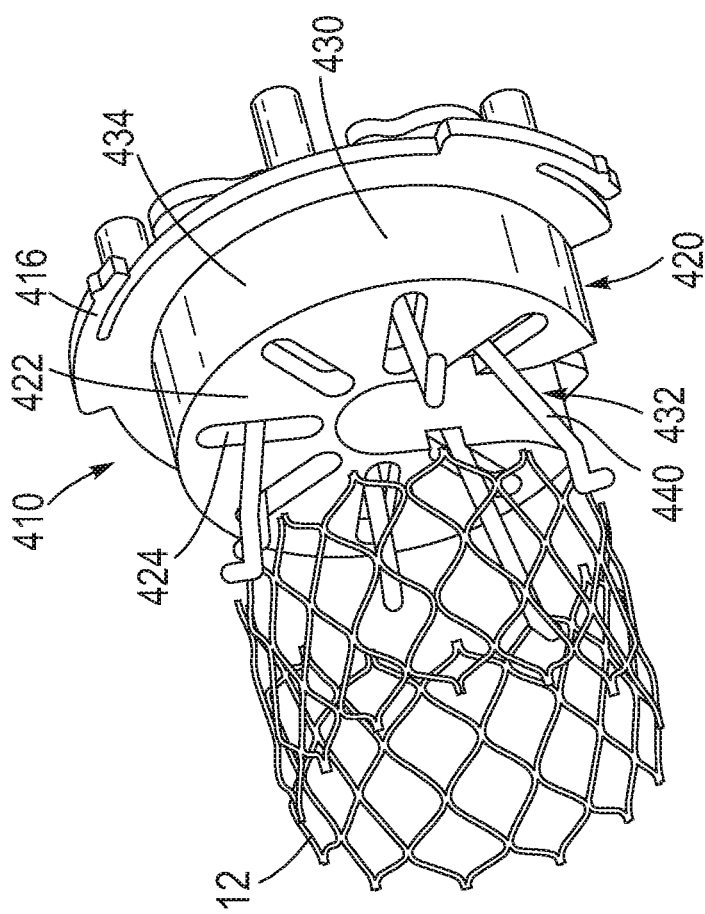
FIG. 16C is a front perspective view of a frame of a prosthetic heart valve coupled to the holder device depicted in FIG. 16B, according to one embodiment.

The valve retaining member 440 can further include a bias member 458, such as a coil spring as shown in FIG. 16D, configured to urge the first and second legs 444, 446 in a proximal direction. In some embodiments, the bias member 458 can be coupled to the proximal portion 450 of the second leg 446. In other embodiments, the bias member 458 can be coupled to the first leg 444. In yet another embodiment, the bias member 458 can be coupled to both the first and second legs 444, 446. In the illustrated embodiment, the spring is disposed around the first and second legs 444, 446 and one end of the spring abuts an adjacent surface of the base portion 442 and the opposite end of the spring abuts an adjacent surface of the proximal face of the body portion 430 (the proximal face being opposite of the distal face 422). In this manner, the spring exerts a biasing force against the base portion 430 in the proximal direction. When the bias member 458 is in the biased position (e.g., when the spring is fully compressed) and the second leg 446 is engaged with the frame 12, the ledge 448 on the first leg 444 can lean against and engage the distal face 422 to keep the second leg 446 engaged with the frame 12 and prevent proximal movement of the legs 444, 446 against the biasing force of the bias member 458.

Crimping of the prosthetic valve can be achieved by actuation of the crimping device 160 as described above. In some embodiments, the closing jaws 170 of the crimping device 160 can press against about simultaneously both the tip portion 454 of the second leg 446 and the distal end portion 447 of the first leg 444 radially inwardly. Pressing against the tip portion 454 of the second leg 446 can cause the notch 456 to lose grip of the frame 12 and pressing against the distal end portion 447 of the first leg 444 can cause the ledge 448 to be released from the distal face 422.

When the ledge 448 is released from the distal face 422, the bias member 458 is also released and can thus return to its unbiased position. The bias member 458 can push against the base portion 442 in the proximal direction, thus causing the legs 444, 446 of the valve retaining member 440 to move proximally relative to the valve alignment portion 420 to a location proximal of the frame 12. When all the valve retaining members 440 are moved out of the interior space of the frame 12, the prosthetic heart valve can be fully crimped to the compressed configuration on the delivery apparatus.

In other embodiments, the closing jaws 170 of the crimping device 160 can press against only the tip portion 454 of the second leg 446 radially inwardly (and causing the notch 456 to lose grip of the frame 12) without pressing against the distal end portion 447 of the first leg 444. For example, when the closing jaws 170 apply enough force to the tip portion 454 of the second leg 446, the first leg 444 can also be radially deflected such that the ledge 448 can be released from the distal face 422. In some embodiments, radial deflection of the first leg 444 can be caused by the transmission of the force applied to the tip portion 454 of the second leg 446 through the base portion 442. In another embodiment, when the second leg 446 is sufficiently deflected by the crimping force, the deflected second leg 446 can press against the first leg 444, causing the first leg 444 to deflect.

Assembly Packaging

In the following, the holder device 110 is used as an example to describe the assembly packaging, although it should be understood that other holder devices (e.g., 210, 310, and 410) described above can also be used following the same principles.

In some embodiments, the prosthetic heart valve 10 in the expanded configuration can be pre-coupled to the holder device 110 by the manufacturer. The assembly comprised of the holder device 110 and the prosthetic heart valve 10 pre-coupled to the holder device can be placed inside a container for shipment to a distributor or end user.

Figure 13:
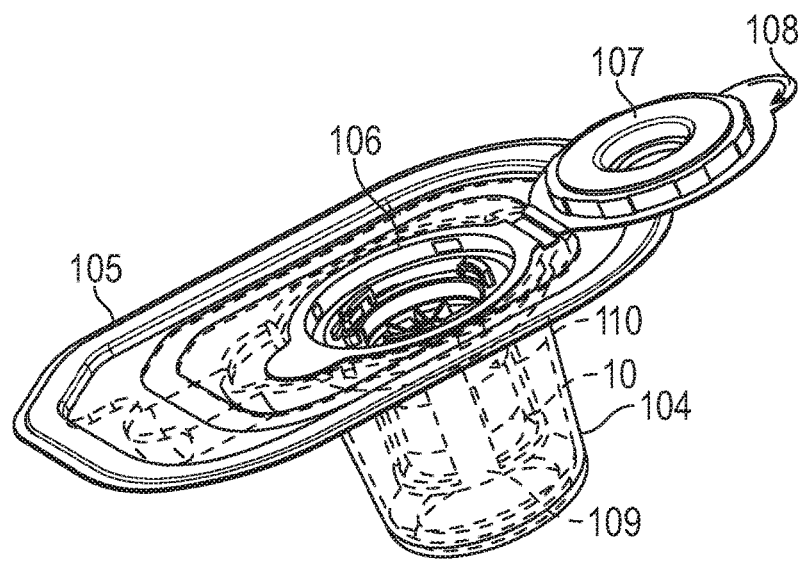
FIG. 13 shows a perspective view of a container that includes an assembly comprised of a holder device and a prosthetic heart valve, according to another embodiment.

FIG. 13 shows one embodiment of a container 104. In some embodiments, the container 104 can be connected to a flange 105. As depicted, the container 104 can have an upper opening 106 which can be closed by a hinged cap 107 with a pull tab 108. Alternatively, the container can have a threaded opening which can be closed by a threaded cap (not shown). The container 104 can include an anchoring mechanism 109 (e.g., an interior scaffold or frame structure) that is configured to releasably secure the holder device 110 inside the container 104 such that the holder device 110, once it is coupled to the anchoring mechanism, cannot move relative to the container 102. Thus, the container 104 can be used for safe storage and transportation of the assembly of the holder device 110 and the prosthetic heart valve 10.

The container 104 (including the cap 107) can be configured to be leak proof and/or air tight. In an exemplary embodiment, the container 104 can be filled with a preservative/hydrating solution, such that the holder device 110 and the prosthetic heart valve 10 retained therein can be submerged in the preservative/hydrating solution. In particular, in certain embodiments, it is desirable to keep the leaflets 18 of the prosthetic valve submerged in the preservative solutions during shipping and storage. After the manufacturing process and before implantation, the prosthetic heart valve 10 can be preconditioned as the valvular structure (leaflets) requires, together with the holder device 110.

Figure 14:
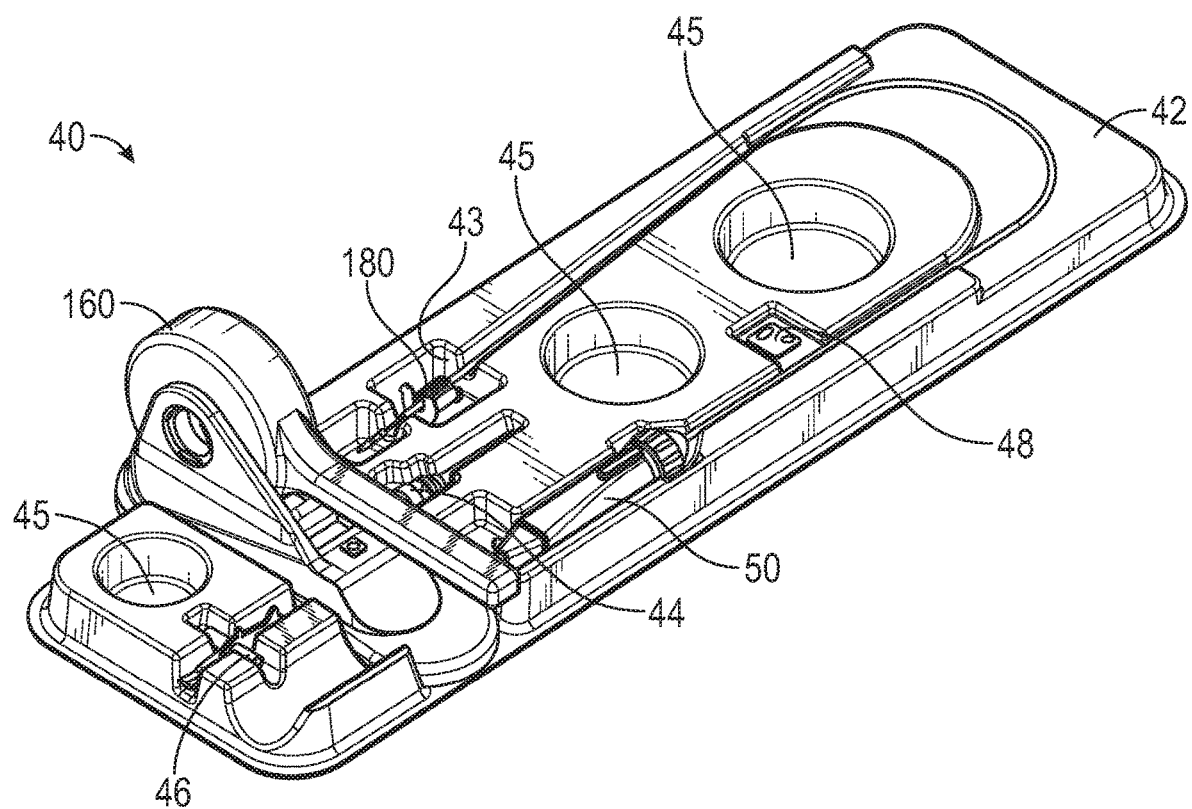
FIG. 14 shows a packaging assembly that contains a plurality of devices that can be used for implanting a prosthetic heart valve.

FIG. 14 shows an exemplary packaging assembly 40 (which can also be referred to as a "toolkit") that can include one or more components. As depicted, the packaging assembly 40 can include a tray 42 having a plurality of recesses 43 that are configured to retain, without limitation, one or more of the following devices: a delivery apparatus 50, a crimping device 160, a positioning device 180, a loader 44, a syringe 46 for injecting an inflation fluid into the port 53 for inflating the balloon 54, a timer 48, etc.

As shown, the positioning device 180 can be pre-mounted onto the shaft of the delivery apparatus 50. In addition, the tray 42 can contain one or more recesses or wells 45 configured to hold contrast saline solution and/or the heparinized saline solution as needed. The tray 42 along with the various components held within the tray and can be sterilized and contained within an enclosure (such as a sealed plastic enclosure) that maintains a sterile environment inside the enclosure during shipping and storage. In other embodiments, the packaging assembly 40 can also include the container 104 which retains the prosthetic heart valve 10 and the holder device 110.

In some embodiments, the prosthetic valve and the holder device assembly can be pre-coupled to the positioning device 180, which can be pre-mounted to the delivery apparatus as shown in FIG. 14. The prosthetic valve, the holder device, and the positioning device and the distal end portion of the delivery apparatus can be contained within a wet storage compartment that contains a hydrating fluid for the leaflets of the prosthetic valve, with the wet storage compartment being contained within a larger dry storage compartment containing the other components shown in FIG. 14.

As noted above, the leaflets 18 of the prosthetic valve (typically made from bovine pericardium tissue or other natural or synthetic tissues) can be "dry leaflets" that are treated during the manufacturing process so that they are completely or substantially dehydrated and can be stored without a hydrating fluid. As used herein, "dry" or "substantially dry" means that all or almost all of the interstitial water has been removed from the tissue. Methods for treating tissue leaflets for dry storage are disclosed in U.S. Pat. No. 8,007,992 and U.S. Patent Publication No. 2009/0164005; filed Dec. 18, 2008, both of which documents are incorporated herein by reference.

When the prosthetic valve includes dry tissue leaflets, the prosthetic valve can be pre-coupled to the holder device HO, which in turn can be pre-coupled to the positioning device 180, which in turn can be pre-mounted on the delivery apparatus 50. All of these components can be packaged together in the same sterile, dry enclosure.

Also, as discussed previously, in embodiments where the prosthetic valve, the holder device, and the positioning device are all mounted on the delivery apparatus for shipping and storage, the holder device and the positioning device can be two, non-separable portions of a larger holder and positioning device.

In addition to the embodiments described above, the following list of numbered examples are also within the scope of this disclosure.

LIST OF EXAMPLES

1. An assembly, comprising: a holder device; and a non-self-expandable prosthetic heart valve being radially compressible from an expanded configuration to a compressed configuration; wherein the holder device is configured to hold the prosthetic heart valve in the expanded configuration and to allow the prosthetic heart valve to be inserted in a crimping device so that the prosthetic heart valve can be crimped onto a valve mounting portion of a delivery apparatus.

2. The assembly of example 1, wherein the holder device comprises one or more retaining members configured to secure the prosthetic heart valve to the holder device when the prosthetic heart valve is in the expanded configuration and configured to release the prosthetic heart valve from the holder device when the prosthetic heart valve is compressed from the expanded configuration to the compressed configuration on the valve mounting portion of the delivery apparatus.

3. The assembly of example 2, wherein a distal portion of each retaining member extends distally into the prosthetic heart valve when the prosthetic heart valve is in the expanded configuration, and wherein the distal portion of each retaining member is disposed proximal to the prosthetic heart valve when the prosthetic heart valve is in the compressed configuration.

4. The assembly of any of the examples 2-3, wherein each of the retaining members has a protrusion extending radially outwardly at a distal end of the retaining member, and wherein each protrusion is configured to extend radially outwardly into an opening of the prosthetic heart valve when the prosthetic heart valve is in the expanded configuration.

5. The assembly of any of the examples 2-4, wherein the holder device comprises a first portion and a second portion, and wherein the one or more retaining members extend distally from the second portion and are axially moveable relative to a distal face of the first portion.

6. The assembly of example 5, wherein the prosthetic heart valve elongates unidirectionally when the prosthetic heart valve is crimped from the expanded configuration to the compressed configuration such that the prosthetic heart valve can elongate distally while the distal face of the first portion prevents proximal elongation of the prosthetic heart valve.

7. The assembly of any of the examples 5-6, wherein the retaining members are configured to extend distally relative to the distal face of the first portion for coupling to the prosthetic heart valve in the expanded configuration, and move proximally relative to the distal face of the first portion after releasing the prosthetic heart valve when the prosthetic heart valve is radially compressed.

8. The assembly of example 7, wherein when the prosthetic heart valve is held by the holder device, a proximal end portion of the prosthetic heart valve abuts the distal face of the first portion when the prosthetic heart valve is in the expanded configuration and is secured to the holder device by the retaining members.

9. The assembly of any of the examples 5-8, wherein the second portion of the holder device comprises one or more sloped projections corresponding to the one or more retaining members, and wherein each sloped projection interfaces with a sloped member on the corresponding retaining member such that the retaining members can slide distally into an interior space of the prosthetic heart valve when the prosthetic heart valve is in the expanded configuration.

10. The assembly of any of the examples 5-9, wherein the holder device comprises one or more biasing members configured to bias the second portion proximally relative to the first portion.

11. The assembly of any of the examples 5-10, wherein the second portion comprises one or more arms, wherein a distal end of each arm extends distally relative to the distal face of the first portion when the retaining members are coupled to the prosthetic heart valve.

12. The assembly of example 11, wherein at least one arm is circumferentially disposed between a pair of adjacent retaining members, wherein the retaining members extend radially outwardly relative to the arms when the prosthetic heart valve is in the expanded configuration, and wherein the retaining members are compressed radially inwardly and radially align with at least a portion of the arms as the prosthetic heart valve is radially compressed.

13. The assembly of any of the examples 11-12, wherein the distal end of each arm comprises a sloped surface configured to interface with a crimping jaw such that a radially inward movement of the crimping jaw exerts a force to the sloped surface and urges the corresponding arm to move proximally relative to the first portion.

14. The assembly of any of the examples 1-13 further comprising a positioning device configured to be releasably coupled to a shaft of the delivery apparatus and to be releasably coupled to the holder device.

15. The assembly of example 14, wherein the positioning device comprises a body comprising an interior surface defining an axially extending passage that is sized to form an interference fit with a segment of the shaft.

16. The assembly of example 15, wherein the segment of the shaft is located distally by a predefined distance relative to the valve mounting portion.

17. The assembly of any of the examples 15-16, wherein the inner surface of the body comprises a row of a plurality of circumferentially oriented grooves extending from a proximal end of the body to a distal end of the body such that a sterilization gas can permeate into the passage through the plurality of grooves when the body is coupled to the shaft.

18. The assembly of any of the examples 14-17, wherein the holder device comprises one or more first coupling members that are mateable with one or more second coupling members of the positioning device.

19. The assembly of any of the examples 1-18 further comprising the crimping device, which is configured to radial compress the prosthetic heart valve from the expanded configuration to the compressed configuration, wherein the holder device comprises one or more third coupling members that are mateable with one or more fourth coupling members of the crimping device.

20. A system for prosthetic heart valve implantation, the system comprising: a positioning and holder assembly configured to retain a prosthetic heart valve in an expanded configuration, be mounted on a shaft of a delivery apparatus, and allow insertion of the prosthetic heart valve into a crimping device for crimping the prosthetic heart valve from a radially expanded configuration to a radially compressed configuration onto a valve mounting portion of the delivery apparatus.

21. The system of example 20, wherein the positioning and holder assembly comprises a positioning portion configured to be releasably coupled to the shaft of the delivery apparatus and a holder portion configured to be releasably retain the prosthetic heart valve in the radially expanded configuration while the prosthetic heart valve is crimped onto the valve mounting portion of the delivery apparatus.

22. The system of example 21, wherein the positioning portion and the holder portion are separable from each other.

23. The system of example 21, wherein the positioning portion and the holder portion are non-separable from each other.

24. The system of example 21, wherein the holder portion comprises one or more retaining members configured to secure the prosthetic heart valve to the holder portion when the prosthetic heart valve is in the expanded configuration and configured to release the prosthetic heart valve from the holder portion when the prosthetic heart valve is crimped from the expanded configuration to the compressed configuration on the valve mounting portion a the delivery apparatus.

25. The system of example 24, wherein a distal portion of each retaining member extends distally into the prosthetic heart valve when the prosthetic heart valve is in the expanded configuration, and Wherein the distal portion of each retaining member is disposed proximal to the prosthetic, heart valve when the prosthetic heart valve is in the compressed configuration.

26. The system of any of the examples 24-25, wherein each of the retaining members has a protrusion extending radially outwardly at a distal end of the retaining member, and wherein each protrusion is configured to extend radially outwardly into an opening of the prosthetic heart valve when the prosthetic heart valve is in the expanded configuration.

27. The system of any of the examples 24-26, wherein the holder portion comprises a first portion and a second portion, and wherein the one or more retaining members extend distally from the second portion and are axially moveable relative to a distal face of the first portion.

28. The system of example 27, wherein the prosthetic heart valve elongates unidirectionally when the prosthetic heart valve is crimped from the expanded configuration to the compressed configuration such that the prosthetic heart valve can elongate distally while the distal face of the first portion prevents proximal elongation of the prosthetic heart valve.

29. The system of any of the examples 27-28, wherein the plurality of retaining members are configured to extend distally relative to the distal fare of the first portion for coupling to the prosthetic heart valve in the expanded configuration, and move proximally relative to the distal face of the first portion after releasing the prosthetic heart valve when the prosthetic heart valve is radially compressed.

30. The system of example 29, wherein when the prosthetic heart valve is held by the holder portion, a proximal end portion of the prosthetic heart valve abuts the distal face of the first portion when the prosthetic heart valve is in the expanded configuration and is secured to the holder portion by the plurality of retaining members.

31. The system of any of the examples 27-30, wherein the second portion comprises a plurality of sloped projections corresponding to the plurality of retaining members, and wherein each sloped projection interfaces with a sloped member on the corresponding retaining member such that the retaining members can slide distally into an interior space of the prosthetic heart valve when the prosthetic heart valve is in the expanded configuration.

32. The system of any of the examples 27-31, wherein the holder portion comprises one or more biasing members configured to bias the second portion proximally relative to the first portion.

33. The system of any of the examples 27-32, wherein the second portion comprises one or more arms, wherein a distal end of each arm extends distally relative to the distal face of the first portion when the retaining members are coupled to the prosthetic heart valve.

34. The system of example 33, wherein at least one arm is circumferentially disposed between a pair of adjacent retaining members, wherein the retaining members extend radially outwardly relative to the arms when the prosthetic heart valve is in the expanded configuration, and wherein the retaining members are compressed radially inwardly and radially align with at least a portion of the arms as the prosthetic heart valve is radially compressed.

35. The system of any of the examples 33-34, wherein the distal end of each arm comprises a sloped surface configured to interface with a crimping jaw of the crimping device such that a radially inward movement of the crimping jaw exerts a force to the sloped surface and urges the corresponding arm to move proximally relative to the first portion.

36. The system of example 21, wherein the positioning portion comprises a body comprising an interior surface defining an axially extending passage that is sized to form an interference fit with a segment of the shaft.

37. The system of example 36, wherein the segment of the shaft is located distally by a predefined distance relative to the valve mounting portion.

38. The system of any of the examples 36-37, wherein the inner surface of the body comprises a row of a plurality of circumferential oriented grooves extending from a proximal end of the body to a distal end of the body such that a sterilization gas can permeate into the passage through the plurality of grooves when the body is coupled to the shaft.

39. The system of any of the examples 20-38, wherein the positioning and holder assembly further comprises one or more coupling members that are mateable to one or more complimentary coupling members of the crimping device.

40. A method of crimping a prosthetic heart valve onto a delivery apparatus, the method comprising: coupling a crimping device to a positioning and holder assembly mounted on a shaft of a delivery apparatus so that a prosthetic heart valve retained by the positioning and holder assembly is inserted into the crimping device; and actuating the crimping device to radially compress the prosthetic heart valve from an expanded configuration to a compressed configuration and onto a valve mounting portion of the delivery apparatus.

41. The method of example 40 further comprising coupling the prosthetic heart valve in the expanded configuration to the positioning and holder assembly.

42, The method of any of the examples 40-41 further comprising mounting the positioning and holder assembly to a predetermined location on the shaft of the delivery apparatus, wherein the predetermined location is spaced relative to the valve mounting portion of the delivery apparatus.

43. The method of example 42, wherein the positioning and holder assembly comprises a positioning portion releasably coupled to the shaft of the delivery apparatus and a holder portion releasably retaining the prosthetic heart valve.

44. The method of example 43 wherein the act of mounting the positioning and holder assembly comprises coupling the positioning portion to the predetermined location on the shaft of the delivery apparatus, and coupling the holder portion to the positioning device.

45. The method of any of the examples 40-44 wherein the act of actuating the crimping device releases the prosthetic heart valve from the positioning and holder assembly.

46. The method of any of the examples 40-45, wherein the compression of the prosthetic heart valve causes unidirectional elongation of the prosthetic heart valve such that a proximal end portion of the prosthetic heart valve is fixedly aligned with a proximal end of the valve mounting portion and a distal end portion of the prosthetic heart valve extends distally during the compression until it aligns with a distal end of the valve mounting portion when the prosthetic heart valve is in the compressed configuration.

47. The method of any of the examples 40-46, further comprising decoupling the positioning and holder assembly from the delivery apparatus after the prosthetic heart valve is crimped onto the valve mounting portion.

48. The method of example 47, further comprising removing the delivery apparatus, together with the prosthetic heart valve, from the crimping device after the positioning and holder assembly is decoupled from the delivery apparatus.

49. The method of any of the examples 40-48, wherein the positioning and holder assembly comprises one or more retaining members configured to releasably couple to the prosthetic heart valve, and wherein the positioning and holder assembly further comprises one or more arms, wherein each arm extends distally into an interior space of the prosthetic heart valve when the retaining members are coupled to the prosthetic, heart valve.

50. The method of example 49, wherein the act of actuating the crimping device pushes the one or more retaining members radially inwardly so as to decouple the one or more retaining members from the prosthetic heart valve.

51. The method of any of the examples 49-50, wherein the act of actuating the crimping device pushes the one or more arms proximally relative to and away from the prosthetic heart valve.

52. A holder device for a prosthetic heart valve, comprising: one or more retaining members configured to secure a prosthetic heart valve to the holder device when the prosthetic heart valve is in a radially expanded configuration and configured to release the prosthetic heart valve from the holder device when the prosthetic heart valve is compressed with a crimping device from the radially expanded configuration to a radially compressed configuration.

53. The holder device of example 52, wherein each of the retaining members has a protrusion extending radially outwardly at a distal end of the retaining member, and wherein each protrusion is configured to extend radially outwardly into an opening of the prosthetic heart valve when the prosthetic heart valve is in the expanded configuration.

54. The holder device of any of the examples 52-53 wherein a distal portion of each retaining member extends distally into the prosthetic heart valve when the prosthetic heart valve is in the expanded configuration, and wherein the distal portion of each retaining member is disposed proximal to the prosthetic heart valve when the prosthetic heart valve is in the compressed configuration.

55. The holder device of any of the examples 52-54 further comprising a valve alignment portion configured to secure the holder device to the crimping device, and wherein the retaining members are movable relative to a distal face of the valve alignment portion.

56. The holder device of example 55, wherein a proximal end portion of the prosthetic heart valve abuts the distal face of the valve alignment portion when the prosthetic heart valve is in the expanded configuration.

57. The holder device of any of the examples 55-56 further comprising one or more biasing members configured to bias the retaining members proximally relative to the valve alignment portion.

58. The holder device of any of the examples 55-57 further comprising one or more arms, wherein a distal end of each arm extends distally relative to the distal face of the valve alignment portion when the retaining members are coupled to the prosthetic heart valve.

59. The holder device of example 58, wherein at least one arm is circumferentially disposed between a pair of adjacent retaining members, wherein the retaining members extend radially outwardly relative to the arms when the prosthetic heart valve is in the expanded configuration, and wherein the retaining members are compressed radially inwardly and radially align with at least a portion of the arms as the prosthetic heart valve is radially compressed with the crimping device.

60. The holder device of any of the examples 58-59; wherein the distal end of each arm comprises a sloped surface configured to interface with the crimping device such that, upon actuation of the crimping device, the crimping device exerts a force to the sloped surface and urges the corresponding arm proximally relative to the valve alignment portion.

61. A positioning device for positioning a prosthetic heart valve on a delivery apparatus, comprising: a body; one or more coupling members that are mateable with one or more complementary coupling members of a prosthetic heart valve holder device; wherein the body comprises an interior surface defining an axially extending passage that is sized to form an interference fit with a shaft of the delivery apparatus.

62. The positioning device of example 61, wherein the inner surface of the body comprises a row of a plurality of circumferentially oriented grooves extending from a proximal end of the body to a distal end of the body such that a sterilization gas can permeate into the passage through the plurality of grooves when the body is coupled to the shaft.

63. A holder device for a prosthetic heart valve, comprising: a body portion and one or more retaining members, wherein each retaining member comprises a head portion configured to retain the prosthetic heart valve in a radially expanded configuration and a tail portion coupled to a ledge member of the body portion when the prosthetic head portion retains the heart valve in the radially expanded configuration, and wherein the tail portion is configured to decouple from the ledge member when the head portion is compressed radially inwardly so that the prosthetic heart valve is detached from the head portion and can be crimped to a radially compressed configuration.

64. A holder device for a prosthetic heart valve, comprising: a body portion and one or more retaining members, wherein each retaining member comprises a first leg, a second leg and a bias member, wherein the second leg; is configured to retain the prosthetic heart valve in a radially expanded configuration when the first leg engages with the body portion to retain the bias member in a biased configuration, and wherein when the second leg is compressed radially inwardly to release the prosthetic heart valve from the second leg, the first leg is configured to disengage the body portion to release the bias member, which returns to its unbiased configuration that causes the retaining member to move away from the body portion.

General Considerations

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art when viewed in light of this disclosure.

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined. Also, with reference to the holder device 110, the positioning device 180, the crimping device 160, the delivery apparatus 50, and the prosthetic valve 10 (when mounted to the holder device or the delivery apparatus), "proximal" refers to a position, direction, or portion of a device that is closer to the handle of the delivery apparatus and the user, while "distal" refers to a position, direction, or portion of a device that is further away from the handle of the delivery apparatus and the user.

As used herein, the term "approximately" and "about" means the listed value and any value that is within 10% of the listed value. For example, "about 90 degrees" means any value between 81-99 degrees, inclusive.

As used in this application and in the claims, the singular forms "a," "an," and "the" include the plural forms unless the context clearly dictates otherwise. Additionally, the term "includes" means "comprises." Further, the terms "coupled" and "connected" generally mean physically, mechanically, chemically, magnetically, and/or electrically linked and do not exclude the presence of intermediate elements between the coupled or connected items absent specific contrary language.

Directions and other relative references (e.g., inner, outer, etc.) may be used to facilitate discussion of the drawings and principles herein, but are not intended to be limiting. For example, certain terms may be used such as "inside," "outside,", "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. As used herein, "and/or" means "and" or "or", as well as "and" and "or".

In view of the many possible embodiments to which the principles of the disclosure may be applied, it should be recognized that the illustrated embodiments are only examples and should not be taken as limiting the scope of the claimed subject matter. Rather, the scope of the claimed subject matter is defined by the following claims and their equivalents.

We claim:

1. An assembly comprising:
   a holder device; and
   a non-self-expandable prosthetic heart valve being radially compressible from an expanded configuration to a compressed configuration, the prosthetic heart valve comprising an annular frame that is radially compressible and expandable;
   wherein the holder device is configured to hold the prosthetic heart valve in the expanded configuration and to allow the prosthetic heart valve to be inserted in a crimping device so that the prosthetic heart valve can be crimped onto a valve mounting portion of a delivery apparatus,
   wherein the holder device comprises one or more retaining members configured to secure the prosthetic heart valve to the holder device when the prosthetic heart valve is in the expanded configuration and release the prosthetic heart valve from the holder device when the prosthetic heart valve is compressed from the expanded configuration to the compressed configuration on the valve mounting portion of the delivery apparatus,
   wherein each retaining member comprises an axially extending beam and a protrusion extending radially outwardly from a distal end portion of the beam, wherein the beam extends distally into an interior space of the annular frame when the prosthetic heart valve is in the expanded configuration,
   wherein the protrusion extends radially from the interior space of the annular frame, through an open cell of the annular frame, to a location outside of the annular frame when the prosthetic heart valve is in the expanded configuration.

2. The assembly of claim 1, wherein the one or more retaining members move axially relative to the prosthetic heart valve when the prosthetic heart valve is radially compressed from the expanded configuration to the compressed configuration.

3. The assembly of claim 1, wherein the protrusion of each retaining member is disposed proximal to the prosthetic heart valve when the prosthetic heart valve is in the compressed configuration.

4. The assembly of claim 1, wherein the holder device comprises a first portion and a second portion, and wherein the one or more retaining members extend distally from the second portion and are axially moveable relative to a distal face of the first portion.

5. The assembly of claim 4, wherein the prosthetic heart valve elongates unidirectionally when the prosthetic heart valve is crimped from the expanded configuration to the compressed configuration such that the prosthetic heart valve can elongate distally while the distal face of the first portion prevents proximal elongation of the prosthetic heart valve.

6. The assembly of claim 4, wherein the retaining members are configured to extend distally relative to the distal face of the first portion for coupling to the prosthetic heart valve in the expanded configuration, and move proximally relative to the distal face of the first portion after releasing the prosthetic heart valve when the prosthetic heart valve is radially compressed.

7. The assembly of claim 6, wherein when the prosthetic heart valve is held by the holder device, a proximal end portion of the prosthetic heart valve abuts the distal face of the first portion when the prosthetic heart valve is in the expanded configuration and is secured to the holder device by the retaining members.

8. The assembly of claim 4, wherein the second portion of the holder device comprises one or more sloped projections corresponding to the one or more retaining members, and wherein each sloped projection interfaces with a sloped member on the corresponding retaining member such that the retaining members can slide distally into an interior space of the prosthetic heart valve when the prosthetic heart valve is in the expanded configuration.

9. The assembly of claim 4, wherein the holder device comprises one or more biasing members configured to bias the second portion proximally relative to the first portion.

10. The assembly of claim 4, wherein the second portion comprises one or more arms, wherein a distal end of each arm extends distally relative to the distal face of the first portion when the retaining members are coupled to the prosthetic heart valve.

11. The assembly of claim 10, wherein at least one arm is circumferentially disposed between a pair of adjacent retaining members, wherein the retaining members extend radially outwardly relative to the arms when the prosthetic heart valve is in the expanded configuration, and wherein the retaining members are compressed radially inwardly and radially align with at least a portion of the arms as the prosthetic heart valve is radially compressed.

12. The assembly of claim 10, wherein the distal end of each arm comprises a sloped surface configured to interface with a crimping jaw such that a radially inward movement of the crimping jaw exerts a force to the sloped surface and urges the corresponding arm to move proximally relative to the first portion.

13. The assembly of claim 1 further comprising a positioning device configured to be releasably coupled to a shaft of the delivery apparatus and to be releasably coupled to the holder device.

14. The assembly of claim 13, wherein the positioning device comprises a body comprising an interior surface defining an axially extending passage that is sized to form an interference fit with a segment of the shaft.

15. The assembly of claim 14, wherein the segment of the shaft is located distally by a predefined distance relative to the valve mounting portion.

16. The assembly of claim 14, wherein the inner surface of the body comprises a row of a plurality of circumferentially oriented grooves extending from a proximal end of the body to a distal end of the body such that a sterilization gas can permeate into the passage through the plurality of grooves when the body is coupled to the shaft.

17. The assembly of claim 1, further comprising the crimping device, which is configured to radially compress the prosthetic heart valve from the expanded configuration to the compressed configuration, wherein the holder device comprises one or more coupling members that are mateable with corresponding coupling members of the crimping device.

18. A holder device for a prosthetic heart valve, comprising:
one or more retaining members, wherein a distal portion of each retaining member has a protrusion configured to extend radially outwardly through an open cell of an annular frame of the prosthetic heart valve to secure the prosthetic heart valve to the holder device when the prosthetic heart valve is in a radially expanded configuration, wherein the protrusion of each retaining member is pushed radially inwardly into an interior space of the annular frame when pressed by a jaw of a crimping device to release the prosthetic heart valve from the holder device when the prosthetic heart valve is compressed by the crimping device from the radially expanded configuration to a radially compressed configuration,
wherein the one or more retaining members are configured to move axially relative to the prosthetic heart valve as the prosthetic heart valve is radially compressed from the radially expanded configuration to the radially compressed configuration.

19. A holder device for a prosthetic heart valve, comprising:
a first portion and a second portion,
wherein the second portion is axially movable relative to the first portion,
wherein the second portion comprises one or more retaining members, wherein each retaining member is configured to extend into an interior space of an annular frame of the prosthetic heart valve located distal to the first portion and has a protrusion configured to extend radially outwardly through an open cell of the annular frame so as to hold the prosthetic heart valve when the prosthetic heart valve is in an expanded configuration, and
wherein the protrusion of each retaining member is pushed radially inwardly into the interior space of the annular frame by a jaw of a crimping device so as to release the prosthetic heart valve, wherein each retaining member is configured to move axially to a location that is proximal to the prosthetic heart valve when the prosthetic heart valve is radially compressed from the expanded configuration to a compressed configuration.

* * * * *